United States Patent [19]

Adams et al.

[11] Patent Number: 5,411,873
[45] Date of Patent: May 2, 1995

[54] PROCESS FOR PRODUCING HETEROLOGOUS POLYPEPTIDES

[75] Inventors: Robin M. Adams, San Francisco; Scott D. Power, San Bruno; David B. Powers, San Francisco; James A. Wells, San Mateo; Daniel G. Yansura, Pacifica, all of Calif.

[73] Assignee: Genencor, Inc., South San Francisco, Calif.

[21] Appl. No.: 928,697

[22] Filed: Aug. 11, 1992

Related U.S. Application Data

[63] Continuation of Ser. No. 488,433, Feb. 27, 1990, abandoned, which is a continuation of Ser. No. 846,627, Apr. 1, 1986, abandoned, which is a continuation-in-part of Ser. No. 614,612, May 29, 1984, Pat. No. 4,760,025.

[51] Int. Cl.6 ............................................. C12P 21/02
[52] U.S. Cl. .................................. 435/69.1; 435/69.7; 435/69.8; 935/48
[58] Field of Search .................... 435/69.1, 69.7, 172.1, 435/172.3, 199, 212, 320.1, 69.8, 252.31; 935/10, 14, 51, 48, 74; 536/23.4, 23.7

[56] References Cited

U.S. PATENT DOCUMENTS

| | | | |
|---|---|---|---|
| 4,543,329 | 9/1985 | Daum et al. | 935/51 |
| 4,595,658 | 6/1986 | Zinder et al. | 935/48 |
| 4,711,844 | 12/1987 | Chang | 935/51 |
| 4,745,069 | 5/1988 | Mayne et al. | 935/51 |
| 4,760,025 | 7/1988 | Estell et al. | 435/172.3 |
| 4,769,327 | 9/1988 | Stephens et al. | 435/172.3 |

FOREIGN PATENT DOCUMENTS 0130756 1/1985 European Pat. Off. ......... 435/172.3
0158981 4/1985 European Pat. Off. .
0161937 11/1985 European Pat. Off. .

OTHER PUBLICATIONS

Zaghloul et al, Journal of Bacteriology 164 (2) pp. 550–555 (1985).
Vasantha et al, Journal of Bacteriology 159 (3) pp. 811–819 (1984).
Vasantha et al, Journal of Bacteriology 165 (3) pp. 837–842 (1986).

Primary Examiner—James Martinell
Attorney, Agent, or Firm—Robin M. Silva; Richard F. Trecartin; Flehr, Hohbach, Test, Albritton & Herbert

[57] ABSTRACT

Processes for producing various heterologous polypeptides which when expressed are either incorrectly processed and hence asssociated with the surface of the host cell or are not processed to mature form. More specifically, processes for the production of heterologous non-human carbonyl hydrolases expressed either in host cells incapable of producing enzymatically active endoprotease or host cells deficient in enzymatically active extracellular endoprotease are disclosed. Such non-human carbonyl hydrolases generally are incapable of autoproteolytic maturation and become associated with the surface of expression hosts which are deficient in enzymatically active extracellular endoprotease. Processes for preparing non-human carbonyl hydrolase and heterologous polypeptides which are expressed as part of a fusion polypeptide are also disclosed, as well as non-human carbonyl hydrolases which are substantially free of the host cell membrane with which they are normally associated.

22 Claims, 16 Drawing Sheets

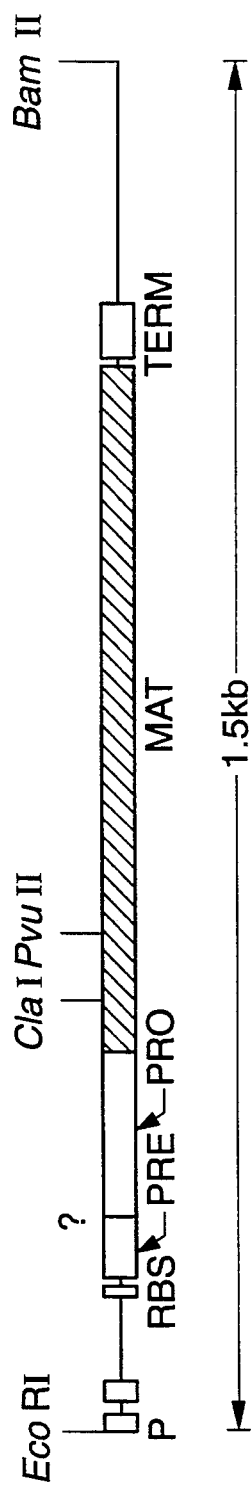
FIG._1A

FIG._1B-1

```
                                                                                              -107
                                                                                              fMet
  ⑤→                                                          RBS                             GTG
1   GGTCTACTAAAATATTATTCCATACTATACAAT TAATAACACAGAATAATCTGTCTATTGGTATTCTGCAAATGAAAAAAGGAGGATAAAGA

P                                   ③→                          ④→

-90
         Arg Gly Lys Lys Val Trp Ile Ser Leu Leu Phe Ala Leu Ile Phe Thr Met Ala Phe Gly Ser Thr Ser
99       AGA GGC AAA AAA GTA TGG ATC AGT TTG CTG TTT GCT TTA GCG TTA ATC TTT ACG ATG GCG TTC GGC AGC ACA TCC
                                            PRE
                                                                                         -60
         -80                                                       PRO
         Ser Ala Gln Ala Ala Lys Lys Ser Asn Gly Glu Phe Val Gly Tyr Lys Lys Gln Thr Met Ser Thr Met
174      TCT GCC CAG GCG GCA AAG AAG TCA AAC GGG GAA TTT GTC TAT AAA AAG CAA ACA ATG AGC ACG ATG

-50                                                     -40
         Ser Ala Ala Lys Lys Asp Val Ser Glu Lys Val Gly Lys Lys Gln Phe Lys Tyr Val Asp Ala
249      AGC GCC GCT AAG AAG GAT GTC TCT GAA AAA GTG GGG AAA AAG CAA TTC AAA TAT GTA GAC GCA

-20                              -10
         Ala Thr Leu Asn Glu Lys Leu Glu Lys Lys Asp Pro Ser Val Ala Pro Ala Leu His Ser Gln
324      GCT ACA TTA AAC GAA AAA TTG GAA AAA AAA GAC CCG AGC GTC GCT CCT CTG CAC TCT CAA
                                   MAT→
                                   1                                10
         Ala His Ala Tyr Ala Gln Ser Val Pro Tyr Gly Val Ser Gln Ile Lys Ala Pro Ala Leu His Ser Gln
         -1
         His Val Ala His Ala Tyr Ala Gln Ser Val Pro Tyr Gly Val Ser Gln Ile Lys Ala Pro Ala Leu His Ser Gln
399      CAC GTA GCA CAT GCG TAC GCG CAG TCC GTG CCT TAC GGC GTA TCA CAA ATT AAA GCT CCT GCT CTG CAC TCT CAA 20                                             30                          40
         Gly Tyr Thr Gly Ser Asn Val Lys Val Ala Val Ile Asp Ser Gly Ile Asp Ser Ser His Pro Asp Leu Lys Val
474      GGC TAC ACT GGA TCA AAT GTT AAA GTA GCG GTT ATC GAC AGC GGT ATC GAT TCT TCT CAT CCT GAT TTA AAG GTA
```

FIG. 1B-2

| Pos | | | | | | | | | | | | | | | |
|---|---|---|---|---|---|---|---|---|---|---|---|---|---|---|---|
| 549 | Ala GCA | Gly GGC | Ala GCA | Ser AGC | 50 Met ATG | Val GTT | Pro CCT | Ser TCT | Glu GAA | Thr ACA | Asn AAT | Pro CCT | Phe TTC | Gln CAA | 60 Asp GAC | Asn AAC | Ser TCT | His CAC | Gly GGA | Thr ACT | His CAC | Val GTT | Ala GCC |
| 624 | 70 Gly GGC | Thr ACA | Val GTT | Ala GCG | Ala GCT | Leu CTT | Asn AAT | Asp GAT | Ala GCA | 80 Gly GGT | Val GTA | Leu TTA | Gly GGC | Val GTT | Ser TCT | Ala GCA | Ala GCA | 90 Leu CTT | Ser TCA | Tyr TAC | Ala GCT | Val GTA | Lys AAA |
| 699 | Val GTT | Leu CTC | Gly GGT | Ile ATT | Asn AAC | Met ATG | Ser AGC | 100 Gly GGT | Gln CAA | Tyr TAC | Ser AGC | Trp TGG | Ile ATT | Asn AAC | Ala GCG | Pro CCA | Ser AGC | 110 Ala GCG | Asn AAC | Asn AAT | Met ATG |
| 774 | 120 Asp GAC | Val GTT | Ile ATT | Asn AAC | Met ATG | Ser AGC | Leu CTC | Gly GGC | Gly GGA | Pro CCT | 130 Ser TCT | Gly GGT | Ser TCT | Ala GCA | Ala GCG | Leu TTA | Lys AAA | Ala GCG | Val GTT | Gly GGC | Tyr TAC | 140 Lys AAA | Asp GAT | Ala GCC | Val GTT | Ala GCA |
| 849 | Ser TCC | Gly GGC | Val GTA | Val GTC | 150 Val GTC | Val GTG | Ala GCA | Ala GCA | Ile ATT | Ala GCA | Ala GCG | Gly GGC | Asn AAC | Ser TCA | 160 Ser TCC | Ser AGC | Ser AGC | Thr ACA | Val GTT | Gly GGC | Ser AGC | Ser TCA | Val GTA | Ala GCA |
| 924 | 170 Lys AAA | Tyr TAC | Pro CCT | Ser TCT | Met ATG | Ala GCT | Val GTA | Ala GCA | Gly GGC | Val GTT | 180 Ala GCA | Val GTA | Asp GAT | Ser AGC | Ser AGC | Asn AAC | Gln CAA | Arg AGA | Ala GCA | 190 Ser TCT | Phe TTC | Lys AAA | Tyr TAC | Gly GGG | Ala GCG | Tyr TAC | Gly GGA | Pro CCT |
| 999 | Glu GAG | Leu CTT | Asp GAT | Val GTC | Met ATG | Ala GCA | Pro CCT | Gly GGC | Val GTA | 200 Ile ATC | Ser TCT | Thr ACG | Leu CTT | Gln CAA | Ser CAA | Thr AGC | Leu CTT | 210 Pro CCT | Gly GGA | Asn AAC | Lys AAA | His CAC | Tyr TAC | Ala GCA | Ala GCC | Tyr TAC | Pro CCT | Gly GGT |
| 1074 | 220 Thr ACG | Ser TCA | Met ATG | Ala GCA | Ser TCT | Pro CCG | His CAC | Val GTT | Ala GCA | Gly GGA | 230 Ala GCG | Ala GCT | Ala GCT | Leu TTG | Ile ATT | Leu CTT | Ser TCT | Lys AAG | His CAC | 240 Pro CCG | Asn AAC | Trp TGG | Thr ACA | Asn AAC | Gly GGT | Asn AAC | Thr ACT |

```
        Gln Val Arg Ser Ser Leu Glu Asn Thr Thr Thr Lys Leu Gly Asp Ser Phe Tyr Tyr Gly Lys Gly Leu Ile Asn
                                250                                           260
1149    CAA GTC CGC AGC AGT TTA GAA AAC ACC ACT ACA AAA CTT GGT GAT TCT TTC TAC TAT GGA AAA GGG CTG ATC AAC

Val Gln Ala Ala Ala Gln Gln OC                 TERM
        270                     275
1224    GTA CAG GCG GCA GCT CAG TAA AACATAAAAAACCGGGCCTTGGCCCCGGGTTTTTATTTTCTTCCTCCGGATGTTCAATCCGCTCC

1316    ATAATCGACGGATGGCTCCCCTGAAAATTTTAACGAGAAACGGGGTTGACCGGCTCAGTCCGTAACGGCCAAGTCCTGAAACGTCTCAATCGCCG

1416    CTTCCCGGGTTCCGGTCAGCTCAATGCCGTAACGGTCGGGCGGTTTCCTGATACCGGGAGACGGCATTCGTAATCGGATC
```

*FIG._1B - 3*

| *FIG._1B - 1* |
| *FIG._1B - 2* |
| *FIG._1B - 3* |

*FIG._1B*

1    GATATACCTAAATAGAGATAAAATCATCTCAAAAAAATGGGTCTACTAAAATATTATTCCATCTATTACAATAAATTCACAGAATAGTCTTTAAGTAAG

101  TCTACTCTGAATTTTTTAAAAGGAGAGGGTAAAGA

|     |       |       |       |       |       |       |       |       |       |       |       |       |       |       |       |       |       |       |       |       |       |       |       |       |       |       |       |
|-----|-------|-------|-------|-------|-------|-------|-------|-------|-------|-------|-------|-------|-------|-------|-------|-------|-------|-------|-------|-------|-------|-------|-------|-------|-------|-------|-------|
|     |       |       |       |       |       |       |       |       |       |       |       |       |       |       |       |       |       |       |       |       | fMet  | Arg   | Ser   | Lys   | Lys   | Leu   | Thr   | Leu   |
|     |       |       |       |       |       |       |       |       |       |       |       |       |       |       |       |       |       |       |       |       | GTG   | AGA   | AGC   | AAA   | AAA   | TTG   | ACG   | TTA   |

185  
-90                                                                                                              -80                                                                                  -70
Ile  Phe  Thr  Met  Ala  Phe  Ser  Asn  Met  Ser                    Ala  Gln  Ala  Ala  Gly  Lys  Lys  Ile  Trp  Ile  Ser  Ser  Leu  Phe  Ala  Leu  Thr  Leu
ATC  TTT  ACG  ATG  GCG  TTC  AGC  AAC  ATG  TCT                    GCG  CAG  GCT  GCC  GGA  AAA  AAA  TTG  TGG  ATC  AGC  AGT  TTG  TTT  GCG  TTA  ACG  TTA

260  
                                 -60                                                                                                                           -50
Gly  Phe  Lys  Gln  Thr  Met  Ser  Ala  Met  Ser                    Ala  Lys  Ala  Lys  Lys  Lys  Ser  Ser  Thr  Glu  Lys  Lys  Tyr  Ile  Val
GGA  TTT  AAA  CAG  ACA  ATG  AGT  GCC  ATG  TCC                    TCC  AAG  GCT  AAG  AAA  AAG  AGT  ACA  GAA  AAG  AAA  TAC  ATT  GTC

335  
-40                                                                                                              -30
Gln  Lys  Gln  Phe  Lys                        Val  Asn  Ala        Ala  Ala  Ala  Ala  Asp  Lys  Lys  Val  Ile  Ser  Glu  Lys  Gly  Gly  Val
CAA  AAG  CAA  TTT  AAG                        GTT  AAC  GCG        GCA  GCC  GCG  GCA  GAT  AAA  AAG  GTA  ATT  TCT  GAA  AAA  GGC  GGA  GTT

410
                                 -10                                                                                                                           -1   1
Pro  Ser  Val  Ala  Tyr  Val  Glu  Glu  Asp  His                    Ile  Ala  His  Glu  Asp  Leu  Tyr  Ala  Gln  Ser  Val  Lys  Glu  Leu  Lys  Lys  Asp
CCG  AGC  GTT  GCA  TAT  GTG  GAA  GAT  CAT                         ATT  GCA  CAT  GAA  TTG  TAT  GCG  CAA  TCT  GTT  AAA  GAA  TTG  AAA  AAA  GAT 485
                    20                                                                                                                           30                                  32                                       10
Ile  Lys  Ala  Pro  Ala  Leu  His  Ser  Gln  Gly  Tyr  Thr  Gly  Ser  Asn  Val  Lys  Val  Ala  Val  Pro  Tyr  Gly  Ile  Asp  Ser  Gly  Ile
ATT  AAA  GCG  CCG  GCT  CTT  CAC  TCT  CAA  GGC  TAC  ACA  GGC  TCT  AAC  GTA  AAA  GTA  GCT  GTT  CCT  TAT  GGC  ATC  GAC  AGC  GGA  ATT

```
560  Asp Ser His Pro Asp Leu Asn Val Arg Gly Gly Ala Ser Phe Val Pro Ser Glu Thr Asn Pro Tyr Gln Asp
     GAC TCT CAT CCT GAC TTA AAC GTC AGA GGA GGA GCA AGC TTC GTA CCT TCT GAA ACA AAC CCA TAC CAG GAC
                     40                                      50                              60

635  Gly Ser Ser His Gly Thr Val Ala Gly Thr Ile Ala Leu Ala Asn Val Leu Gly Ile Tyr Ser Val Gly Val Ser
     GGC AGT TCT CAC GGT ACG GTA GCC GGT ACG ATT GCC CTT GCT AAT GTT CTG GGT ATC TAT TCA GTC GGC GTT AGC
                     64                   70                                      80                110

710  Pro Ser Ala Ser Leu Tyr Ala Val Lys Val Leu Asp Ser Thr Gly Ser Gly Gln Tyr Ser Trp Ile Ile Asn Gly
     CCA AGC GCA TCA TTA TAT GCA GTA AAA GTG CTT GAT TCA ACA GGA AGC GGC CAA TAT AGC TGG ATT ATT AAC GGC
                                90                                 100                            110

785  Ile Glu Trp Ala Ile Ser Asn Met Asp Val Ile Ser Gly Ile Val Val Ser Leu Gly Gly Pro Thr Gly Ser Thr
     ATT GAG TGG GCC ATT TCC AAC AAT AAT GAT GTT ATC GGT ATC GTT GTC AGC CTT GGA GCA CCT ACT GGT TCT ACA
                                       120                            130                         150

860  Lys Thr Val Val Asp Lys Ala Val Ser Ser Gly Ile Val Val Ala Ala Ala Ala Gly Asn Glu Gly Asn Ser Gly
     AAA ACA GTC GAC AAA GCC GTT TCC GGT ATC GTT GTC GCC GCA GCA GCA GGA AAC GAA GGT AAC AGC
                 140                                 150                               180

935  Ser Thr Ser Thr Val Gly Tyr Pro Ala Lys Tyr Pro Ser Thr Ile Ala Val Gly Ala Val Asn Ser Ser Asn Gln
     AGC ACA AGC ACA GTC GGC TAC CCT GCA AAA TAT CCT TCT ACT ATT GCA GTA GGT GCG AAC AGC TCA AGC AAC CAA
                170                                      180                            200              210

1010 Arg Ala Ser Phe Ser Ala Gly Val Met Asp Leu Glu Val Met Ala Pro Gly Val Ser Ile Gln Ser Thr Leu Pro
     AGA GCT TCA TTC TCC AGC GCA GGT GTG ATG GAT CTT GAG GTG ATG GCT CCT GGC GTG TCC ATC CAA AGC ACA CTT CCT
                190                                      200                                 210
```

```
      Gly Gly Thr Tyr Tyr Gly Ala Tyr Asn Gly Thr Ser Met Ala Thr Pro His Val Ala Gly Ala Ala Leu Ile Leu
1085  GGA GGC ACT TAC TAC GGC GCT TAT AAC GGA ACG TCC ATG GCG ACT CCT CAC GTT GCC GGA GCA GCG TTA ATT CTT
                                          220 221                              230                      260
      Ser Lys His Pro Thr Trp Thr Asn Ala Gln Val Arg Asp Arg Leu Glu Ser Thr Ala Thr Tyr Leu Gly Asn Ser
1160  TCT AAG CAC CCG ACT TGG ACA AAC GCG CAA GTC CGT GAT CGT TTA GAA AGC ACT GCA ACA TAT CTT GGA AAC TCT
                  240                                  250
      Phe Tyr Tyr Gly Lys Gly Leu Ile Asn Val Gln Ala Ala Gln OC
1235  TTC TAC TAT GGA AAA GGG TTA ATC AAC GTA CAA GCA GCT GCA CAA TAA TAGTAAAAAGAAGCAGGTTCCTCCATACCTGCTTC
                      270
1318  TTTTTATTGTCAGCATCCTGATGTTCCGGCATTCTCTTCTTCTCCGGCATGTTGAATCCGTTCCATGATCGACGGATGGCTGCCTCTGAAAATCTTC

1418  ACAAGCACCGGAGGATCAACCTGCTCAGCCCCGTCACGGCCAAATCCTGAAACGTTTAACACTGGCTTCTCTGTTCTCTGTC
```

| FIG.\_2A |
| FIG.\_2B |
| FIG.\_2C |

FIG.\_3

| FIG.\_3A |
| FIG.\_3B |
| FIG.\_3C |

```
CACATGACAC TTGACTCATC TTGATATTAT TCAACAAAAA CAAACACAGG ACAATACTAT CAATTTGTC TAGTTATGTT AGTTTTTGTT GAGTATTCCA
                                                                                                    10
                                                                            1   met gly leu val ser arg
                                                                                ATG GGT TTA GTT TCT CGT
GAATGCTAGT TAATATAAC AATATAAAGT TTTCAGTATT TTCAAAAAGG GGGATTTATT 20                                          30                                    60
val ala ser phe met ser leu ser pro gly val gln ala gly lys leu lys glu
GTC GCT TCG TTT ATG AGT TTA TCA CCA GGT GTT CAG GCT GGT AAG TTG AAA GAG
                                      50
                40                      glu         ile               his gln leu lys
asn gln thr asn phe lys asn ser ile ala gln ser leu    pro      phe      CAT CAG CTT AAA
AAT CAA ACA AAT TTC AAA AAC AGC ATT GCG CAA CTC GAA    CCG      TTT
                                                                                        80
gln phe leu lys asn ile phe arg tyr lys gly asp pro ser lys val ser asn asp ala val
CAG TTT TTG AAA AAC ATT TTT CGA TAT AAA GGT GAC CCT TCC AAA AGC GTG AAT GAC GCT GTC
                90                                 100                              110
asp ala leu tyr lys his phe ala pro glu asn gly val pro ile lys val
GAT GCC CTT TAC AAG CAC TTT GCA CCT GAA AAC GGA GTG CCA ATT AAA GTG
                                   asn                              ser thr thr ile
                                   AAT                              AGC ACG ACT ATC
                                                                                    130
val his val asp asn ser val glu asn gly leu ala lys asp ser ala thr
GTT CAC GTC GAT AAT TCT GAA AAT GGT TTA GCT AAA GAT TCG GCA ACA
                                                          lys ala    ser
                                                          AAA GCT    TCT
                        120                                              150                    160
asn ser gln lys val asp asn tyr val ala leu ala leu his asn gly glu leu    lys    gly    pro asp ala val
AAC AGC CAA AAA GTC GAT AAT TAT GTC GCA CTG GCA CAC AAT GGT GAA TTA    AAA    GGC    CCA GAC GCT GTT
                140                                                      phe                ser lys thr asp
                val                                                      TTC                TCA AAA ACA GAT
                GTC
asn
AAC
```

| ser TCT | asn AAC | gly GGA | ala GCG | ala GCC | lys AAA | asn AAC | ser AGC | asn AAT | 170 lys AAA | ala GCC | glu GAA | leu TTA | glu GAA | thr ACA | lys AAA | 180 asp GAC | gly GGC | ser AGC | tyr TAT | arg CGT | leu CTT |
|---|---|---|---|---|---|---|---|---|---|---|---|---|---|---|---|---|---|---|---|---|---|
| ala GCT | tyr TAC | asp GAC | val GTG | 190 thr ACG | ile ATT | arg CGC | tyr TAT | val GTC | glu GAG | pro CCT | 200 ala GCA | asn AAC | ile ATA | trp TGG | glu GAA | val GTT | asp GAC | ala GCC | glu GAA | thr ACA | 210 gly GGC |
| ser AGC | ile ATT | leu TTA | lys AAA | gln CAG | gln CAA | asn AAT | lys AAA | val GTA | 220 glu GAA | his CAT | pro CCT | Mature ala GCC | ala GCC | thr ACT | gly GGA | ser AGC | 230 thr ACG | leu CTA | lys AAG | gly GGC | ala GCA | thr ACT |
| val GTT | pro CCT | leu TTG | asn AAC | ile ATC | ser TCT | tyr TAT | gly GGA | glu GAA | lys AAA | val GTT | tyr TAT | val GTT | leu CTA | ala GCC | ala GCC | thr ACA | pro CCA | lys AAA | ser TCA | gly GGA | thr ACC | 260 ile ATC |
| ile ATC | thr ACA | tyr TAT | asp GAT | leu TTG | gln CAA | asn AAC | arg AGA | gln CAA | glu GAA | 270 ser AGC | arg CGC | gln CAA | asn AAC | leu CTA | leu CTT | leu CTT | val GTC | 280 ser AGC | thr ACA | thr ACG | gln CAA | thr ACA |
| ser TCT | ser TCA | gln CAG | arg CGG | ala GCA | ala GCA | asp GAC | val GTT | ala GCC | 290 his CAC | leu CTC | tyr TAT | lys AAA | val GTG | 300 gly GGT | thr ACG | lys AAA | thr ACA | 310 phe TTT |
| lys AAA | arg CGA | asn AAC | ser AGC | tyr TAT | asp GAT | asn AAC | val GTT | ser TCT | ile ATC | 320 lys AAA | ser AGT | lys AAA | tyr TAC | ser TCA | val GTG | his CAC | tyr TAC | asp GAT | tyr TAT | tyr TAT | tyr TAT | gly GGT | gln CAA | phe TTT |

Note: The table format above may have column mis-groupings; source is a sequence-coding figure.

FIG. 3C

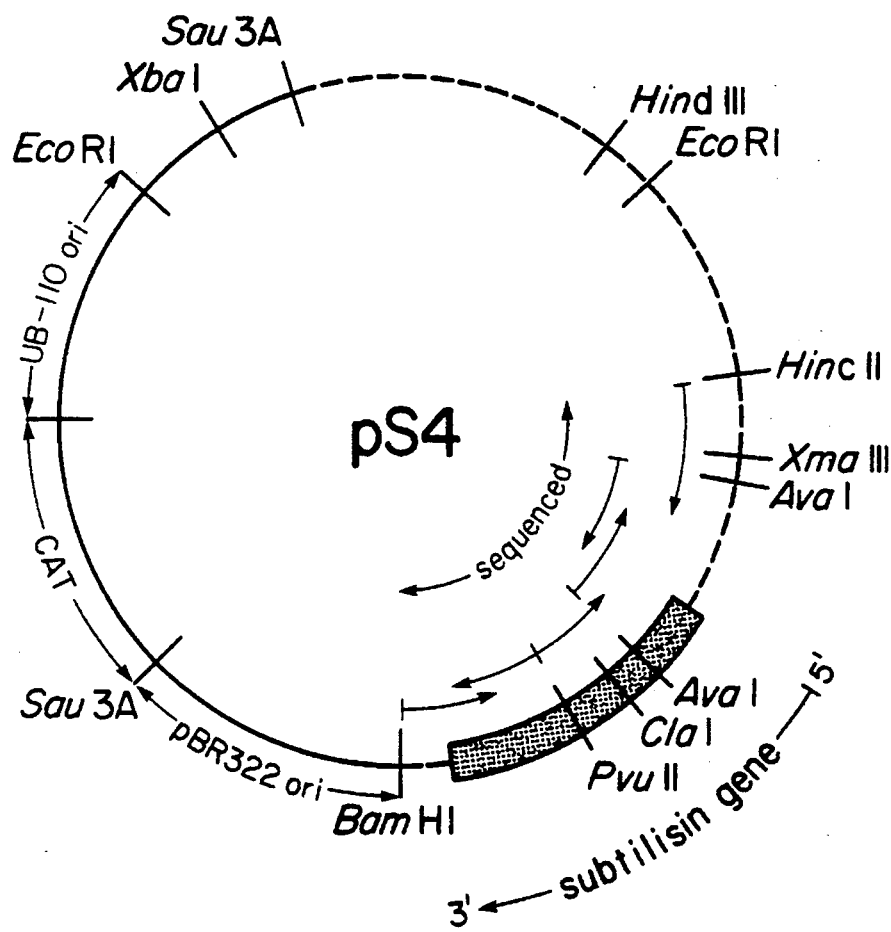
FIG._4
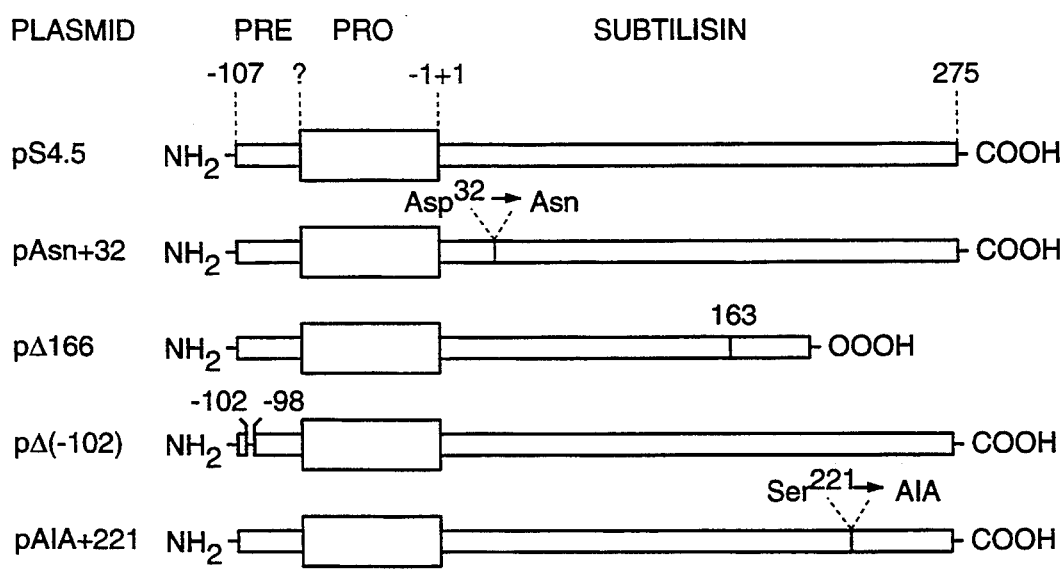
FIG._6

```
codon:                                  220   222                                            230

Wild Type amino acid sequence:          Ala Tyr Asn Gly Thr Ser Met Ala Ser Pro His Val Ala Gly Ala Ala 1. Wild Type DNA sequence:              5'-GCG TAC AAC GGT ACG TCA ATG GCA TCT CCG CAC GTT GCC GGA CCG GCT-3'
                                        3'-CGC ATG TTG CCA TGC AGT TAC CGT AGA GGC GTG CAA CGG CCT CGC CGA-5'

*                            *   *
2. p221 DNA sequence:                   5'GCGnTAC AAC GGT ACC TCA----------CG CAC GCT GCA GGA GCG GCT-3'
                                        3'-CGC ATG TTG CCA TGG AGT          CG GTG CGA CGT CCT CGC CGA-5'
                                                          KpnI                       PstI

*
3. p221 cut with KpnI and PstI:         5'-GCG TAC AAC GGT AC                    pGGA GCG GCT-3'
                                        3'-CGC ATG TTG Cp                      A CGT CCT CGC CGA-5'

*
4. cut p221 ligated with                5'-GCG TAC AAC GGT ACG GCT ATG GCA TCT CCG CAC GTT GCA GGA GCG GCT-3'
   oligonucleotide pools:               3'-CGC ATG TTG CCA TGC CGA TAC CGT AGA GGC GTG CAA CGT CCT CGC CGA-5'
```

FIG._5

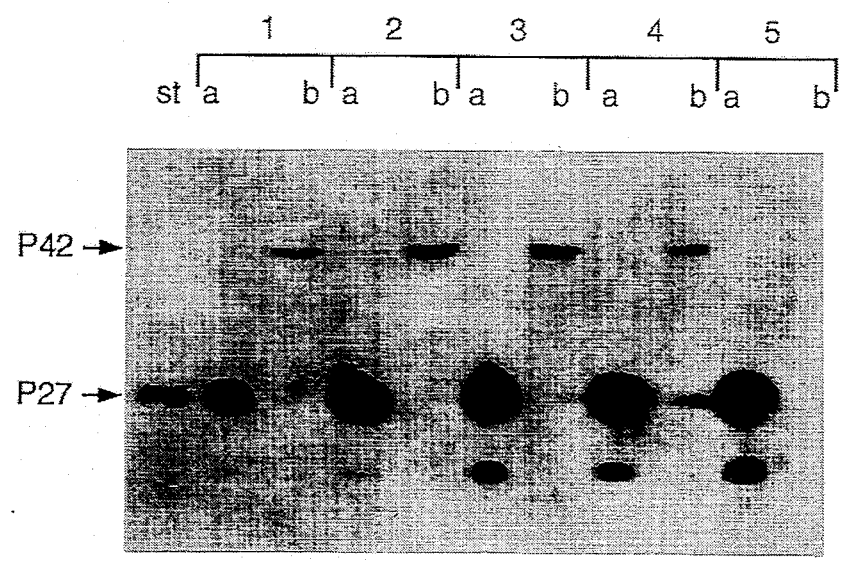
FIG._7
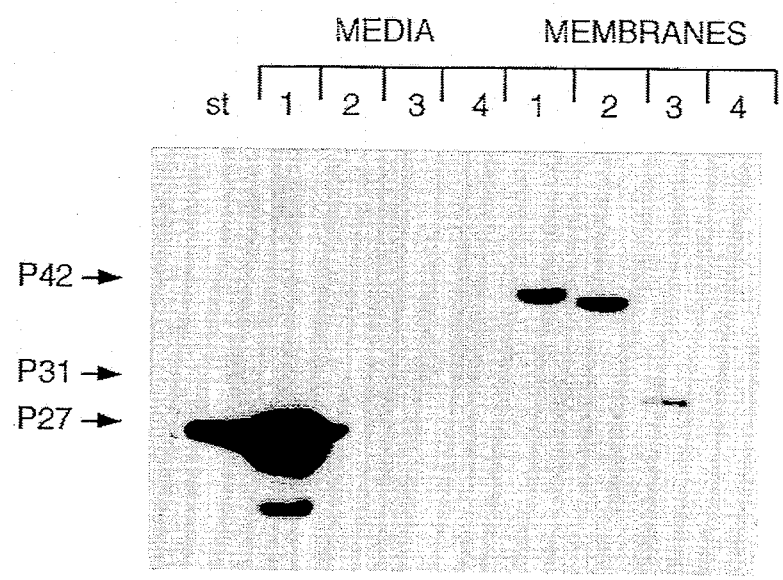
FIG._9

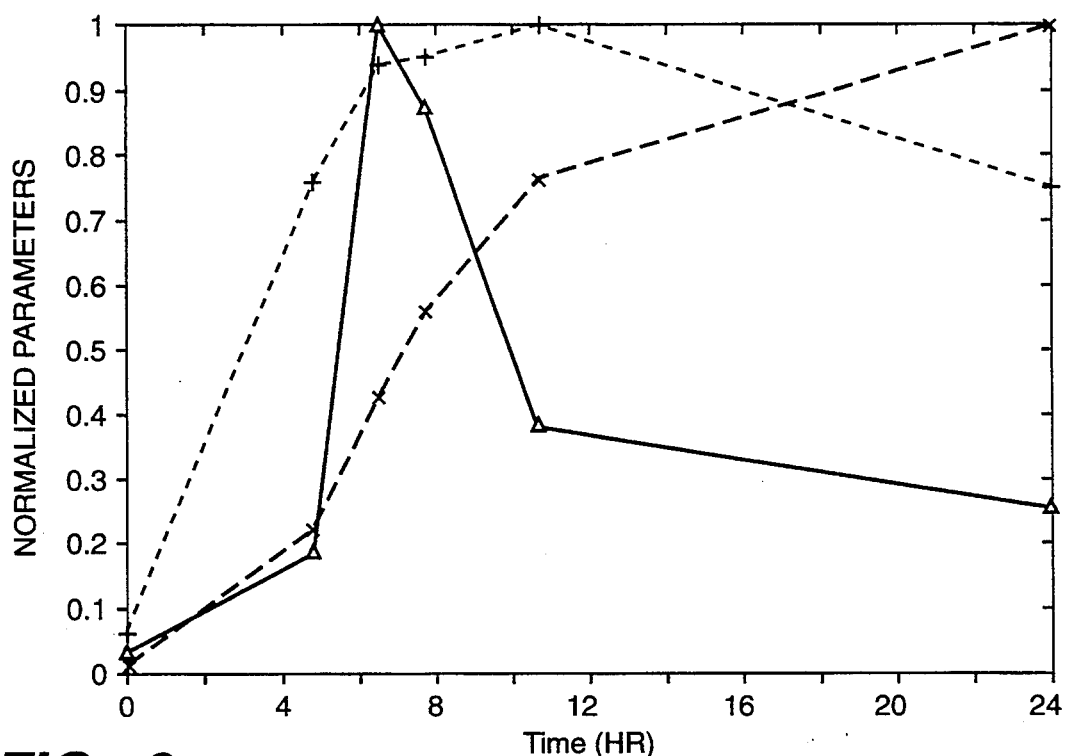
FIG._8
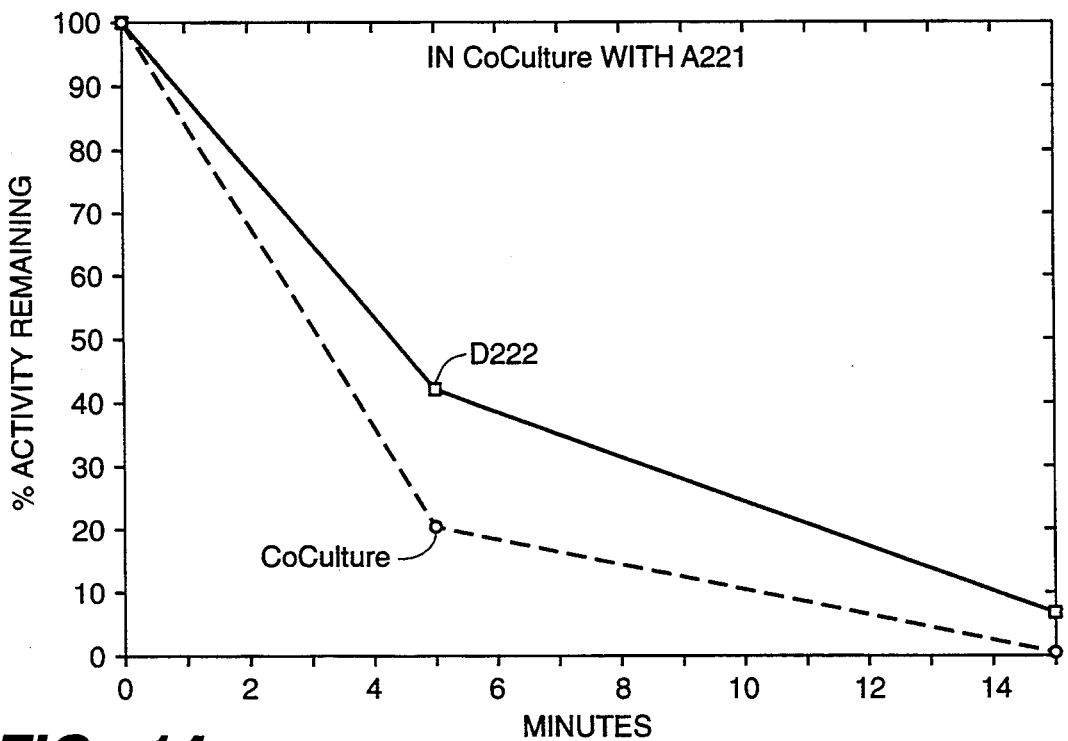
FIG._14

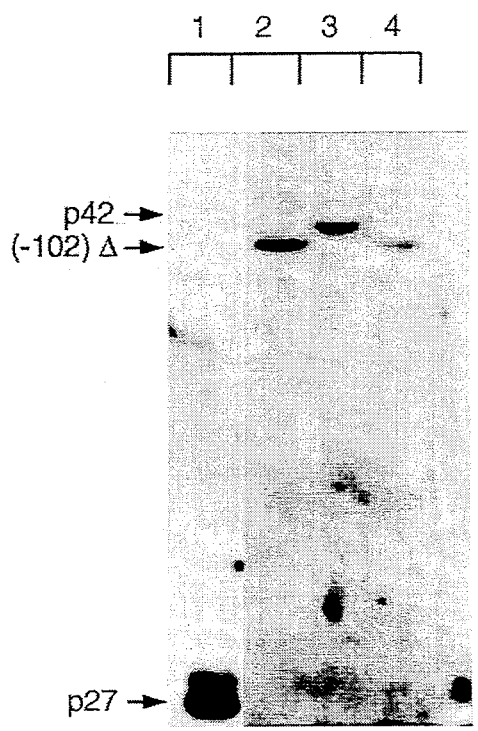
FIG._10
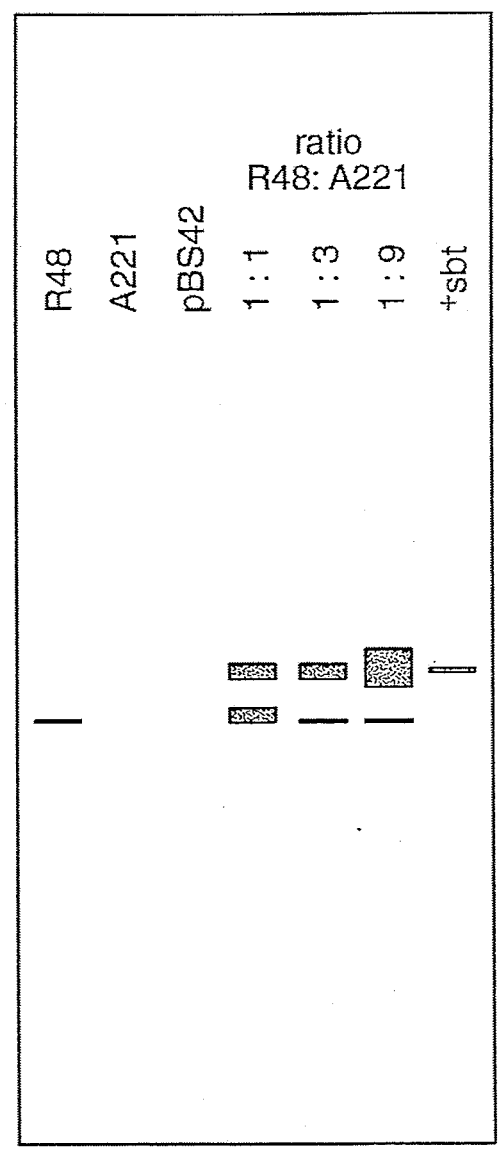
FIG._13
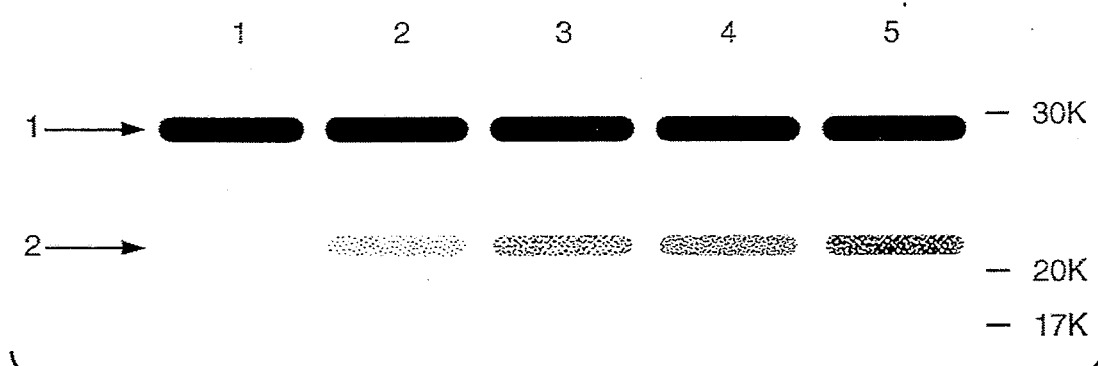
FIG._15

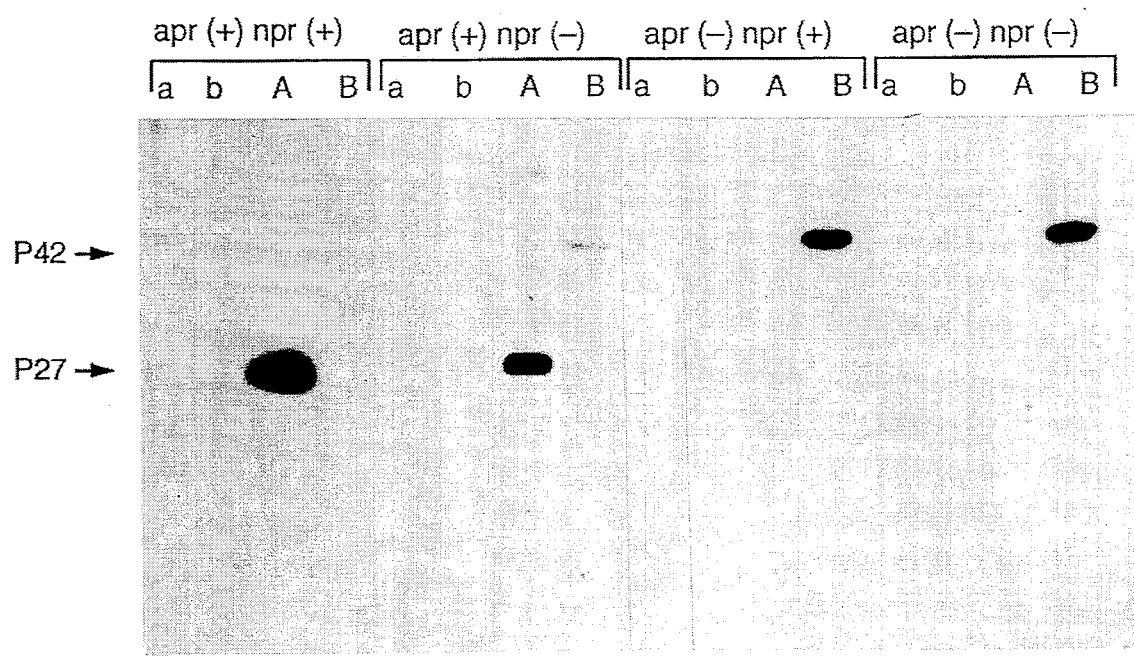
FIG._11
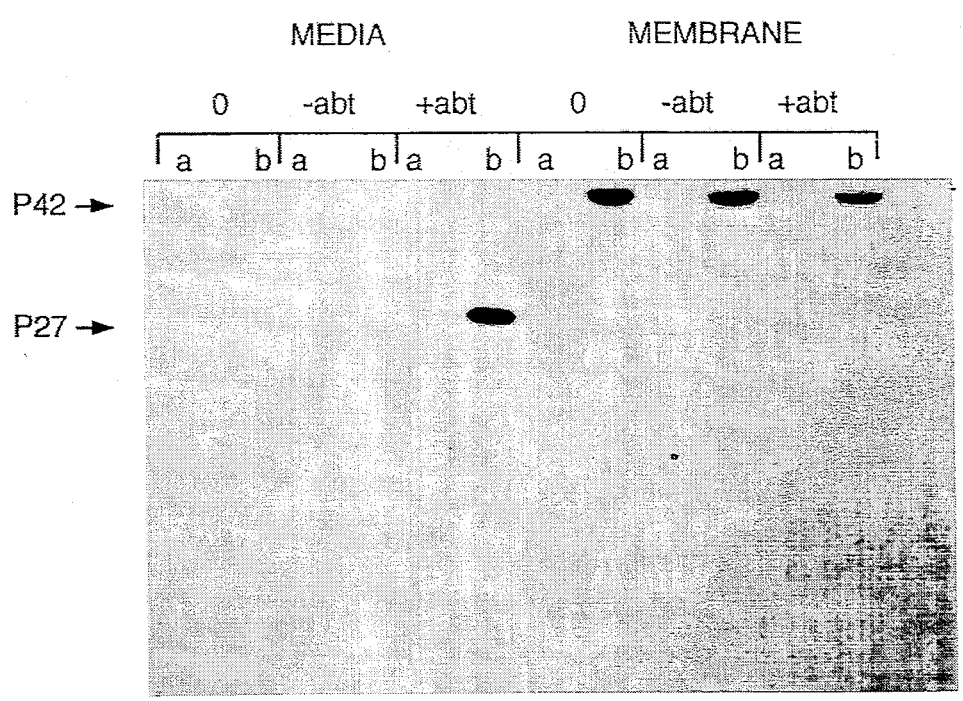
FIG._12

PROCESS FOR PRODUCING HETEROLOGOUS POLYPEPTIDES

This application is a continuation of U.S. application Ser. No. 07/488,433, filed Feb. 27, 1990, now abandoned, which is a continuation of 06/846,627, filed Apr. 1, 1986, now abandoned, which is a continuation in part of U.S. application Ser. No. 06/614,612, filed May 29, 1984, which issued as U.S. Pat. No. 4,760,025 on Jul. 26, 1988, each of which is incorporated herein by reference.

FIELD OF THE INVENTION

The present invention relates to processes for producing various heterologous polypeptides which when expressed are either incorrectly processed and hence become associated with the surface of the host cell or are not processed to mature form. More specifically, the invention relates to processes for the production of heterologous non-human carbonyl hydrolases expressed either in host cells capable of producing enzymatically active endoprotease or in host cells deficient in enzymatically active extracellular endoprotease. Such non-human carbonyl hydrolases generally are incapable of autoproteolytic maturation and become associated with the surface of expression hosts which are deficient in enzymatically active extracellular endoprotease.

The invention also relates to processes for preparing heterologous polypeptides which are expressed as part of a fusion polypeptide as well as non-human carbonyl hydrolases which are substantially free of the host cell membrane with which said hydrolases are normally associated.

BACKGROUND OF THE INVENTION

Various bacteria are known to secrete proteases at some stage in their life cycles. Bacillus species produce two major extracellular proteases, a neutral protease (a metalloprotease inhibited by EDTA) and an alkaline protease (or subtilisin, a serine endoprotease). Both generally are produced in greatest quantity after the exponential growth phase, when the culture enters stationary phase and begins the process of sporulation. The physiological role of these two proteases is not clear. They have been postulated to play a role in sporulation (J. Hoch, (1976) Adv. Genet. 18, 69–98; P. Piggot, et al., (1976) Bact. Rev. 40, 908–962; and F. Priest, (1977) Bact. Rev. 41, 711–753), to be involved in the regulation of cell wall turnover (L. Jolliffe, et al., (1980) J. Bact. 141, 1199–1208), and to be scavenger enzymes (Priest, Id.). The regulation of expression of the protease genes is complex. They appear to be coordinately regulated in concert with sporulation, since mutants blocked in the early stages of sporulation exhibit reduced levels of both the alkaline and neutral protease. Additionally, a number of pleiotropic mutations exist which affect the level of expression of proteases and other secreted gene products, such as amylase and levansucrase (Priest, Id.).

Subtilisin has found considerable utility in industrial and commercial applications (see U.S. Pat. No. 3,623,957 and J. Millet, (1970) J. Appl. Bact. 33, 207). For example, subtilisins and other proteases are commonly used in detergents to enable removal of protein-based stains. They also are used in food processing to accommodate the proteinaceous substances present in the food preparations to their desired impact on the composition.

Classical mutagenesis of bacteria with agents such as radiation or chemicals has produced a plethora of mutant strains exhibiting different properties with respect to the growth phase at which protease excretion occurs as well as the timing and activity levels of excreted protease. These strains, however, do not approach the ultimate potential of the organisms because the mutagenic process is essentially random, with tedious selection and screening required to identify organisms which even approach the desired characteristics. Further, these mutants are capable of reversion to the parent or wild-type strain. In such event the desirable property is lost. The probability of reversion is unknown when dealing with random mutagenesis since the type and site of mutation is unknown or poorly characterized. This introduces considerable uncertainty into the industrial process which is based on the enzyme-synthesizing bacterium. Finally, classical mutagenesis frequently couples a desirable phenotype, e.g., low protease levels, with an undesirable character such as excessive premature cell lysis.

Special problems exist with respect to the proteases which are excreted by Bacillus. For one thing, since at least two such proteases exist, screening for the loss of only one is difficult. Additionally, the large number of pleiotropic mutations affecting both sporulation and protease production make the isolation of true protease mutations difficult.

Temperature sensitive mutants of the neutral protease gene have been obtained by conventional mutagenic techniques, and were used to map the position of the regulatory and structural gene in the *Bacillus subtilis* chromosome (H. Uehara, et al., (1979) J. Bact. 139, 583–590). Additionally, a presumed nonsense mutation of the alkaline protease gene has been reported (C. Roitsch, et al., (1983) J. Bact. 155, 145–152).

Bacillus temperature sensitive mutants have been isolated that produce inactive serine protease or greatly reduced levels of serine protease. These mutants, however, are asporogenous and show a reversion frequency to the wild-type of about from $10^{-7}$ to $10^{-8}$ (F. Priest, Id. p. 719). These mutants are unsatisfactory for the recombinant production of heterologous proteins because asporogenous mutants tend to lyse during earlier stages of their growth cycle in minimal medium when compared to sporogenic mutants, thereby prematurely releasing cellular contents (including intracellular proteases) into the culture supernatant. The possibility of reversion also is undesirable since wild-type revertants will contaminate the culture supernatant with excreted proteases.

Bacillus sp. have been proposed for the expression of heterologous proteins, but the presence of excreted proteases and the potential resulting hydrolysis of the desired product has retarded the commercial acceptance of Bacillus as a host for the expression of heterologous proteins. *Bacillus megaterium* mutants have been disclosed that are capable of sporulation and which do not express a sporulation-associated protease during growth phases. However, the assay employed did not exclude the presence of other proteases, and the protease in question is expressed during the sporulation phase (C. Loshon, et al., (1982) J. Bact. 150, 303–311). This, of course, is the point at which heterologous protein would have accumulated in the culture and be vulnerable.

Accordingly, an object of U.S. Pat. application Ser. No. 614,615 (EPO Publication No. 0130756) is the construction of a Bacillus strain which is substantially free of extracellular neutral and alkaline protease during all phases of its growth cycle and which exhibits substantially normal sporulation characteristics. The need disclosed therein is for a non-revertible, otherwise normal protease deficient organism that can be transformed with high copy number plasmids for the expression of heterologous or homologous proteins.

The present inventors have discovered that certain mutant subtilisins (made according to the methods disclosed in EPO Publication No. 0130756) were not completely secreted from Bacillus expression hosts which were rendered incapable of expressing and secreting enzymatically active neutral protease and subtilisin. These mutant subtilisins, containing mutations within the active site of subtilisin, were found to be incapable of autoproteolytic maturation and thus were bound to the Bacillus cell membrane making them far more difficult to isolate than if they were completely secreted into the culture medium. The inventors discovered that such mutants can be released from the surface of such Bacillus expression hosts by contacting the host cells with an enzymatically active subtilisin.

Accordingly, an object of the invention herein is to provide processes for producing a heterologous non-human carbonyl hydrolase which is not secreted but which is bound to the surface of an expression host which does not produce extracellular enzymatically active subtilisin.

In addition, an object of the invention is to provide processes for producing heterologous non-human carbonyl hydrolases which are released from the surface of a host cell by an enzymatically active subtilisin produced by the host cell.

A further object of the present invention is to provide processes for preparing heterologous polypeptides from a fusion polypeptide which can be cleaved to produce a desired heterologous polypeptide.

Still further an object of the present invention is to provide non-human carbonyl hydrolases which are normally membrane-associated and not released from the host cell expressing the hydrolase. Such hydrolases are substantially free of the host cell membrane with which they are normally associated.

SUMMARY OF THE INVENTION

The invention includes processes for isolating heterologous non-human carbonyl hydrolases which are bound to the surface of an expression host which does not secrete enzymatically active endoprotease. The process comprises expressing a prepro form of heterologous non-human carbonyl hydrolase in a host cell which permits the prepro hydrolase to be transported to the surface of the host cell but not its release in mature form. The heterologous carbonyl hydrolase is removed from the surface of the host cell either by the addition of enzymatically active exogenous subtilisin or by co-culturing such expression host cells with a second cell line which is capable of secreting enzymatically active subtilisin. The bound heterologous carbonyl hydrolase thereby is released into the culture medium from which it may be readily isolated.

In addition, it includes processes for producing heterologous non-human carbonyl hydrolases from host cells which produce a different enzymatically active subtilisin which is capable of releasing the carbonyl hydrolase from the surface of the host cell.

The invention also comprises processes for preparing a heterologous polypeptide expressed as part of a fusion polypeptide. First, a fusion polypeptide is expressed which has an amino-terminal first sequence and a carbonyl-terminal second sequence corresponding to the desired heterologous polypeptide. The fusion polypeptide is capable of being cleaved by subtilisin at a recognition site at the junction of the first and second sequences of the fusion polypeptide or within the first sequence of the fusion polypeptide. This fusion polypeptide is then contacted with a subtilisin which is capable of cleaving the fusion polypeptide at the recognition site.

The invention also includes non-human carbonyl hydrolases which are normally membrane-associated and normally not released from the surface of the host cell expressing the hydrolase. Such carbonyl hydrolase are extracellular and are substantially free of the host cell membrane with which the hydrolase is normally associated.

BRIEF DESCRIPTION OF THE DRAWINGS

FIG. 1 shows the sequence of a functional *B. amyloliquefaciens* subtilisin gene.

In FIG. 1A, the entire functional sequence for *B. amyloliquefaciens*, including the promoter and ribosome binding site, are present on a 1.5 kb fragment of the *B. amyloliquefaciens* genome.

FIG. 1B shows the nucleotide sequence of the coding strand, correlated with the amino acid sequence of the protein. Promoter (p) ribosome binding site (rbs) and termination (term) regions of the DNA sequence as well as sequences encoding the presequence (PRE) putative prosequence (PRO) and mature form (MAT) of the hydrolase are also shown.

FIG. 2 is the sequence of a functional *B. subtilis* subtilisin gene.

FIG. 3 is the nucleotide sequence for a *B. subtilis* neutral protease gene.

FIG. 4 shows the restriction analysis of the subtilisin expression plasmid (pS4). pBS42 vector sequences (4.5 kb) are shown in solid while the insert sequence (4.4 kb) containing the *B. amyloliquefaciens* subtilisin gene is shown dashed.

FIG. 5 discloses the mutagenesis of subtilisin by the substitution of serine at position 221 with alanine.

FIG. 6 shows the various substitutions and deletions of preprosubtilisin disclosed herein.

FIG. 7 is a Western blot of media and membrane fractions of pS4–5.

FIG. 8 shows cell growth and the secretion and membrane accumulation of subtilisin in its various forms as a function of time.

FIG. 9 is a Western bloth of media and membrane fractions demonstrating the localization of mutant subtilisin encoded by pAsn+32 and pα166.

FIG. 10 is a high resolution Western blot analysis of signal peptide deletion mutant pΔ(−102).

FIG. 11 is a Western blot of media and membrane fraction demonstrating the localization of mutant subtilisin encoded by pAsn+32 as expressed by various expression hosts.

FIG. 12 is a Western blot demonstrating the effect of exogenous subtilisin on the membrane-bound mutant subtilisin Asn+32.

FIG. 13 demonstrates the effect of co-culturing BG2036 transformed with pAla221 with a subtilisin secreting organism.

FIG. 14 depicts the activity of mutant subtilisin D222 as a function of time at 50° C. after co-culturing.

FIG. 15 is an immuno-blot demonstrating in vitro cleavage of the fusion polypeptide prosubtilisin -hGH by subtilisin.

DETAILED DESCRIPTION

Carbonyl hydrolases are enzymes which hydrolyze compounds containing

bonds in which X is oxygen or nitrogen. They included naturally occurring carbonyl hydrolases and mutant carbonyl hydrolases. Naturally occurring carbonyl hydrolases principally include hydrolases, e.g. lipases and peptide hydrolases, e.g. subtilisins or metalloproteases. Peptide hydrolases include α-aminoacylpeptide hydrolase, peptidylaminoacid hydrolase, acylamino hydrolase, serine carboxy-peptidase, metallocarboxypeptidase, thiol proteinase, carboxylproteinase and metalloproteinase. Serine, metallo, thiol and acid proteases are included, as well as endo and exo-proteases.

"Mutant carbonyl hydrolase" refers to a carbonyl hydrolase in which the DNA sequence encoding the naturally occurring carbonyl hydrolase is modified to produce a mutant DNA sequence which encodes the substitution, insertion or deletion of one or more amino acids in the carbonyl hydrolase amino acid sequence. Suitable modification methods are disclosed herein and in EPO Publication No. 0130756.

Subtilisins are carbonyl hydrolases which generally act to cleave peptide bonds of proteins or peptides. As used herein, "subtilisin" means a naturally occurring subtilisin or a mutant subtilisin. A series of such naturally occurring proteases is known to be produced and often secreted by various bacterial species. Amino acid sequences of the members of this series are not entirely homologous, however, the proteins in this series exhibit the same or similar type of proteolytic activity. This class of serine proteases shares a common amino acid sequence defining the catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus is aspartate-histidine-serine. In the chymotrypsin related proteases the relative order, however, is histidine-aspartate-serine. Thus, subtilisin herein bears a functional definition—i.e., it refers to a serine protease directly or indirectly associated with or related to a bacterial source.

"Mutant subtilisin" refers to a subtilisin in which the DNA sequence encoding the subtilisin is modified to produce a mutant DNA sequence which encodes the substitution, deletion, or insertion of one or more amino acids in the subtilisin amino acid sequence. Suitable methods to produce such modification include those disclosed herein and in EPO Publication No. 0130756. It is to be understood, however, that subtilisin mutants containing a change in the content or relative order of the catalytic triad, as defined above, are still mutant subtilisins. Thus, for example, a mutant subtilisin having an amino acid sequence which resembles a chymotrypsin related protease is a subtilisin mutant as herein defined.

A subtilisin which is "enzymatically active" is one which is capable of cleaving either the prosequence normally associated with such a subtilisin or the prosequence of the heterologous non-human carbonyl hydrolases as hereinafter defined.

Carbonyl hydrolases and their genes may be obtained from many procaryotic and eucaryotic organisms. Suitable examples of procaryotic organisms include gram negative organisms such as E. coli or pseudomonas and gram positive bacteria such as micrococcus or bacillus. Examples of eucaryotic organisms from which carbonyl hydrolase and their genes may be obtained include yeast such as S. cerevisiae, fungi such as Aspergillus sp., and non-human mammalian sources such as, for example, Bovine sp. from which the gene encoding the carbonyl hydrolase rennin can be obtained. A series of carbonyl hydrolases can be obtained from various related species which have amino acid sequences which are not entirely homologous between the member of that series but which nevertheless exhibit the same or similar type of biological activity. Thus, carbonyl hydrolase as used herein has a functional definition which refers to serine proteases which are associated, directly or indirectly, with procaryotic and non-human eucaryotic sources.

The "non-human carbonyl hydrolases" of the present invention include the mature forms of carbonyl hydrolases as well as subtilisins which are derived from non-human sources. Such hydrolases, in addition, either lack endoprotease activity or are incapable of autoproteolytic maturation. Thus, the non-human carbonyl hydrolases are functionally defined as any heterologous non-human carbonyl hydrolase which either is incorrectly processed by a host cell expressing the same and thus not released from the surface of such host cell or which is produced by such host cells but not processed to the mature form of the carbonyl hydrolase.

"Polypeptides" are polymers of α-amino acids which are covalently linked through peptide bonds. Polypeptides include low molecular weight polymers as well as high molecular weight polymers more commonly referred to as proteins. In addition, a polypeptide can be a phosphopolypeptide, glycopolypeptide or metallopolypeptide. Further, one or more polymer chains may be combined to form a polypeptide.

"Heterologous" refers to non-human carbonyl hydrolases or other polypeptides which are not ordinarily produced by the host cell. Such heterologous polypeptides thus may comprise polypeptides which either do not have substantial amino acid sequence homology with those proteins produced by the host cell (e.g., protein from unrelated procaryotes or protein from eucaryotes such as yeast, fungi and other higher eucaryotes expressed in procaryotes) or may comprise polypeptides with substantial but incomplete homology to proteins produced by the host cell or the cell line from which the host cell is derived. For example, a mutant B. subtilis subtilisin containing a single amino acid substitution as compared to wild-type B. subtilis subtilisin is heterologous whether expressed in a B. subtilis expressing wild-type subtilisin or a mutant B. subtilis strain which does not produce enzymatically active wild-type subtilisin.

"Prosequence" refers to a sequence of amino acids bound to the N-terminal portion of the mature form of a carbonyl hydrolase or other polypeptide which when removed results in the appearance of the "mature" form of the carbonyl hydrolase. Many proteolytic enzymes are found in nature as translational proenzyme products and, in the absence of post-translational processing, are expressed in this fashion. The preferred prosequence is the putative prosequence of *B. amyloliquifaciens* subtilisin although other subtilisin prosequences may be used. The prosequence of *B. amyloliquifaciens* subtilis, was discovered by the inventors to be autolytically cleaved by naturally occuring subtilisin. This discovery was based on the observation that mutant subtilisins which are enzymatically inactive become associated with the surface of the expression host rather than being completely secreted into the expression host medium.

A "signal sequence" or "presequence" refers to any sequence of amino acids bound to the N-terminal portion of a carbonyl hydrolase or other polypeptide or to the N-terminal portion of a prohydrolase or other propolypeptide which may participate in the secretion of the mature or pro forms of the hydrolase or other polypeptide. This definition of signal sequence is a functional one, meant to include all those amino acid sequences, encoded by the N-terminal portion of the subtilisin gene or other secretable carbonyl hydrolases, which participate in the effectuation of the secretion of subtilisin or other carbonyl hydrolases under native conditions. The present invention comprises the harnessing of said sequences to effect resultant partial or complete secretion of any heterologous carbonyl hydrolase or other polypeptide as defined herein.

A "prepro" form of a heterologous carbonyl hydrolase consists of the mature form of the hydrolase having a prosequence operably linked to the amino-terminal first part of the hydrolase and a "pre" or "signal" sequence operably linked to the amino terminal part of the prosequence.

The prepro forms of the heterologous non-human carbonyl hydrolases in one aspect of the invention, are not completely processed to the mature form of hydrolase and thus are not secreted from the host cell expressing the same. This is believed to result from the absence of or decrease in enzymatic activity of the mature form of the carbonyl hydrolase expressed. Such enzymatically inactive hydrolases typically are mutants containing the substitution, deletion or insertion of one or more amino acids of the wild type carbonyl hydrolase. This effect is observed for certain mutant subtilisins which are expressed in a prepro form in host cells which do not secrete enzymatically active endoprotease. As a result, the carbonyl hydrolase, presumably in its prepro form, is transported across the host cell membrane to become bound to the cell membrane or otherwise associated with the surface of the host cell (e.g., by association with the carbohydrate or glycoprotein of the cell membrane). Carbonyl hydrolases which are associated with the surface of an expression host, however, are not limited to mutant subtilisins but rather include all non-human carbonyl hydrolases which are associated with the surface of an expression host and which can be released therefrom by cleavage with subtilisin.

A "fusion" polypeptide comprises at least two parts: an amino terminal first sequence and a carboxyl terminal second sequence comprising the amino acid sequence of a heterologous non-human carbonyl hydrolase or other heterologous polypeptide as defined herein. Examples of heterologous polypeptides include human growth hormone (hGH), tissue plasminogen activator (t-PA), and the subtilisins defined herein. The fusion polypeptide is capable of being cleaved by subtilisin or mutant subtilisin at a recognition site at the junction of the first and second sequences of the fusion polypeptide or at some point within the first sequence. The particular amino acid sequence comprising the first sequence of the fusion polypeptide is preferably the prosequence of *B. amyloliquifaciens* subtilisin although other subtilisin prosequences may be used. However, various other sequences which may be uniquely recognized and cleaved by mutant subtilisins are also included within the scope of this amino-terminal first sequence. The amino acid sequence used in the first sequence of the fusion polypeptide may thus be defined functionally as an amino acid sequence which when combined with a heterologous polypeptide to form a fusion polypeptide results in a fusion polypeptide which is capable of being cleaved by a subtilisin at the recognition site. Such cleavage produces either the mature heterologous polypeptide or non-human carbonyl hydrolase or the mature form of the hydrolase or polypeptide with one or more amino acids from the first sequence sequence attached to the amino terminus.

"Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

The "host cells" used in one aspect of the present invention generally are procaryotic or eucaryotic hosts which preferably have been manipulated by the methods disclosed in EPO Publication No. 0130756 to render them incapable of secreting enzymatically active endoprotease. Host cells are transformed or transfected with vectors constructed using recombinant DNA techniques. Such vectors encode the heterologous non-human carbonyl hydrolases or heterologous polypeptides of the invention and are capable of replication and expression of such hydrolases or polypeptides. A preferred host cell for expressing such hydrolases is the Bacillus strain BG2036 which is deficient in enzymatically active neutral protease and alkaline protease (subtilisin). The construction of strain BG2036 is described in detail in EPO Publication No. 0130756 and further described by Yang, M. Y., et al. (1984) J. Bacteriol. 160, 15–21. Such host cells are distinguishible from those disclosed in PCT Publication No. 03949 wherein enzymatically inactive mutants of intracellular proteases in *E. coli* are disclosed. In the case of host cells which produce an enzymatically active endoprotease to release the heterologous non-human carbonyl hydrolase from the surface of the host cell, *B. subtilisin* I-168 and BG2044 each of which produce active alkaline protease are preferred. Stahl, M. L. and Ferrari, E. (1984) J. Bacteriol. 158, 411–418; Yang, M. Y., et al. (1984) J.

Bacteriol. 160, 15–21. However, other host cells known to those skilled in the art may also be used in practicing the process of the present invention.

"Operably linked" when describing the relationship between two DNA regions simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the carbonyl hydrolase may be obtained in accord with the general methods described in EPO Publication No. 0130756 published Jan. 9, 1985. As can be seen from the examples disclosed therein, the methods generally comprise synthesizing labelled probes having putative sequences encoding regions of the hydrolase of interest, preparing genomic libraries from organisms expressing the hydrolase, and screening the libraries for the gene of interest by hybridization to the probes. Positively hybridizing clones are then mapped and sequenced.

The cloned carbonyl hydrolase is then used to transform a host cell in order to express the hydrolase. The hydrolase gene is then ligated into a high copy number plasmid. This plasmid replicates in hosts in the sense that it contains the well-known elements necessary for plasmid replication: a promoter operably linked to the gene in question (which may be supplied as the gene's own homologous promotor if it is recognized, i.e., transcribed, by the host), a transcription termination and polyadenylation region (necessary for stability of the mRNA transcribed by the host from the hydrolase gene in certain eucaryotic host cells) which is exogenous or is supplied by the endogenous terminator region of the hydrolase gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosonal limitations. However, it is within the scope herein to integrate multiple copies of the hydrolase gene into host genome. This is facilitated by procaryotic and eucaryotic organisms which are particularly susceptible to homologous recombination. The resulting host cells are termed recombinant host cells.

Once the carbonyl hydrolase gene has been cloned, a number of modifications are undertaken to enhance the use of the gene beyond synthesis of the wild type or precursor enzyme. A precursor enzyme is the enzyme prior to its modification as described in this application and in EPO Publication No. 0130756. Usually the precursor is the enzyme as expressed by the organism which donated the DNA modified in accord herewith. The term "precursor" is to be understood as not implying that the product enzyme was the result of manipulation of the precursor enzyme per se but rather of the DNA encoding the precursor enzyme.

In the first of these modifications, the gene may be deleted from a recombination positive (rec+) organism containing a homologous gene. This is accomplished by recombination of an in vitro deletion mutation of the cloned gene with the genome of the organism. Many strains of organisms such as *E. coli* and Bacillus are known to be capable of recombination. All that is needed is for regions of the residual DNA from the deletion mutant to recombine with homologous regions of the candidate host. The deletion may be within the coding region (leaving enzymatically inactive polypeptides) or include the entire coding region as long as homologous flanking regions (such as promoters or termination regions) exist in the host. Acceptability of the host for recombination deletion mutants is simply determined by screening for the deletion of the transformed phenotype. This is most readily accomplished in the case of carbonyl hydrolase by assaying host cultures for loss of the ability to cleave a chromogenic substrate otherwise hydrolyzed by the hydrolase.

Transformed hosts containing the protease deletion mutants are useful for synthesis of products which are incompatible with proteolytic enzymes. These hosts by definition are incapable of secreting enzymatically active extracellular endoprotease encoded by the deleted protease genes described herein. In the case of Bacillus sp. these host cells also are substantially normally sporulating. In addition, the other growth characteristics of the transformants are substantially like the parental organism. Such organisms are useful in that it is expected they will exhibit comparatively less inactivation of heterologous proteins than the parents. Moreover, these hosts have growth characteristics which are superior to known protease-deficient organisms. However, the deletion of neutral protease and subtilisin as described in this application does not remove all of the proteolytic activity of Bacillus. It is believed that intracellular proteases which are not ordinarily excreted extracellularly "leak" or diffuse from the cells during late phases of the culture. These intracellular proteases may or may not be neutral protease or subtilisin as defined herein. Accordingly, the novel Bacillus strains herein are incapable of excreting the subtilisin and/or neutral protease enzymes which ordinarily are excreted extracellularly in the parent strains. "Incapable" means not revertible to the wild type. Reversion is a finite probability that exists with the heretofore known protease-deficient, naturally occurring strains since there is no assurance that the phenotype of such strains is not a function of a readily revertible mutation, e.g. a point mutation. This to be contrasted with the extremely large deletions provided herein.

Figure 3C:
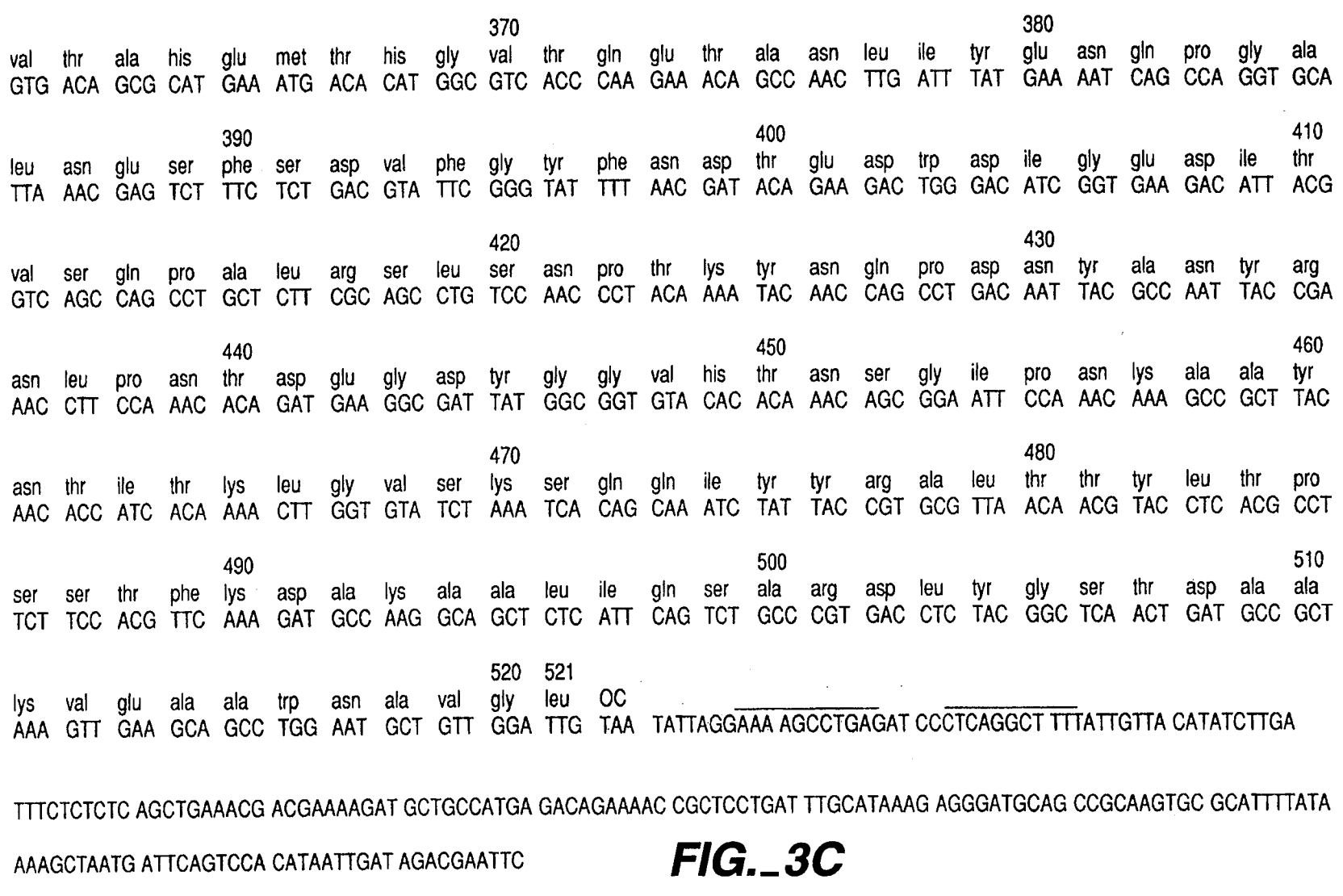

The deletion mutant-transformed host cells herein are free of genes encoding enzymatically active neutral protease or subtilisin, which genes are defined as those being substantially homologous with the genes set forth in FIGS. 1, 2 or 3 as well as the subtilisin sequences disclosed by Svendsen, et al. (1983) Carlberg Res Commun 48, 583–591, and Melourn, et al. FEBS, 183,195–200. "Homologous" genes contain coding regions capable of hybridizing under high stringency conditions with these sequences.

The strains containing carbonyl hydrolase deletion mutants are useful in at least two principal processes. First, they are advantageous in the fermentative production of products ordinarily expressed by a host that are desirably uncontaminated with the protein encoded by the deletion gene. An example is fermentative synthesis of amylase, where contaminant proteases interfere in many industrial uses of amylase. These novel strains relieve the art from part of the burden of purifying such products free of contaminating carbonyl hydrolases.

In a second process, protease deletion-mutant strains are useful in the synthesis of protein which is not otherwise encoded by the strain. These proteins will fall within one of two classes. The first class consists of proteins encoded by genes exhibiting no substantial pretransformation homology with those of the host cell or the organism from which the host cell was derived. These may be proteins from procaryotes as well as eucaryotic proteins from yeast or higher eucaryotic organisms. The novel strains herein serve as useful hosts for expressible vectors containing genes encoding such proteins because the probability for proteolytic degradation of the expressed, heterologous proteins is reduced.

The second class, which is particularly relevant to the invention, consists of mutant host genes exhibiting substantial pretransformation homology with those of the host cell or organism from which the host cell is derived. These include mutations of non-human carbonyl hydrolases such as subtilisin and neutral protease. When so mutated, this group of polypeptides are heterologous to the host cell as defined herein.

The following method was used to facilitate the construction and identification of such mutants as well as the host cells used in the present invention. First, the gene encoding the hydrolase is obtained and sequenced in whole or in part. Then the sequence is scanned for a point at which it is desired to make a mutation (deletion, insertion or substitution) of one or more amino acids in the expressed enzyme. The sequences flanking this point are evaluated for the presence of restriction sites for replacing a short segment of the gene with an oligonucleotide pool which when expressed will encode various mutants. Since unique restriction sites are generally not present at locations within a convenient distance from the selected point (from 10 to 15 nucleotides), such sites are generated by substituting nucleotides in the gene in such a fashion that neither the reading frame nor the amino acids encoded are changed in the final construction. The task of locating suitable flanking regions and evaluating the needed changes to arrive at two unique restriction site sequences is made routine by the redundancy of the genetic code, a restriction enzyme map of the gene and the large number of different restriction enzymes. Note that if a fortuitous flanking unique restriction site is available, the above method need be used only in connection with the flanking region which does not contain a site.

Mutation of the gene in order to change its sequence to conform to the desired sequence is accomplished by M13 primer extension in accord with generally known methods. Once the gene is cloned, it is digested with the unique restriction enzymes and a plurality of end termini-complementary oligonucleotide cassettes are ligated into the unique sites. The mutagenesis is enormously simplified by this method because all of the oligonucleotides can be synthesized so as to have the same restriction sites, and no synthetic linkers are necessary to create the restriction sites. The number of commercially available restriction enzymes having sites not present in the gene of interest is generally large. A suitable DNA sequence computer search program simplifies the task of finding potential 5' and 3' unique flanking sites. A primary constraint is that any mutation introduced in creation of the restriction site must be silent to the final construction amino acid coding sequence. For a candidate restriction site 5' to the target codon a sequence must exist in the gene which contains at least all the nucleotides but for one in the recognition sequence 5' to the cut of the candidate enzyme. For example, the blunt cutting enzyme SmaI (CCC/GGG) would be a 5' candidate if a nearby 5' sequence contained NCC, CNC, or CCN. Furthermore, if N needed to be altered to C this alteration must leave the amino acid coding sequence intact. In cases where a permanent silent mutation is necessary to introduce a restriction site one may want to avoid the introduction of a rarely used codon. A similar situation of SmaI would apply for 3' flanking sites except the sequence NGG, GNG, or GGN must exist. The criteria for locating candidate enzymes is most relaxed for blunt cutting enzymes and most stringent for 4 base overhang enzymes. In general many candidate sites are available. For the codon-221 target described herein a BalI site (TGG/CCA) would have been engineered in one base pair 5' from the KpnI site. A 3' EcoRV site (GAT/ATC) could have been employed 11 base pairs 5' to the PstI site. A cassette having termini ranging from a blunt end up to a four base-overhang will function without difficulty. In retrospect, this hypothetical EcoRV site would have significantly shortened the oligonucleotide cassette employed (9 and 13 base pairs) thus allowing greater purity and lower pool bias problems. Flanking sites should obviously be chosen which cannot themselves ligate so that ligation of the oligonucleotide cassette can be assured in a single orientation.

It should be noted that the amino acid position numbers referred to herein are those assigned to *B. amyloliquefaciens* subtilisin as seen from FIG. 2. It should be understood that a deletion or insertion in the N-terminal direction from a given position will shift the relative amino acid positions so that a residue will not occupy its original or wild type numerical position. Also, allelic differences and the variation among various procaryotic and eucaryotic species will result in position shifts. For example, position 169 from *B. amyloliquefaciens* subtilisin may not be occupied by glycine in all other bacterial subtilisin. In such cases the new positions for glycine will be considered equivalent to and embraced within the designation glycine+169. The new position for glycine+169 is readily identified by scanning the subtilisin in question for a region homologous to glycine+169 in FIG. 2.

The enzymes herein may be obtained as salts. It is clear that the ionization state of a protein will be dependent on the pH of the surrounding medium, if it is in solution, or of the solution from which it is prepared, if it is in solid form. Acidic proteins are commonly prepared as, for example, the ammonium, sodium, or potassium salts; basic proteins as the chlorides, sulfates, or phosphates. Accordingly, the present application includes both electrically neutral and salt forms of the designated carbonyl hydrolases, and the term carbonyl hydrolase referes to the organic structural backbone regardless of ionization state.

The following disclosure is intended to serve as a representation of embodiments herein, and should not be construed as limiting the scope of this application.

Glossary of Experimental Manipulations

In order to simplify the Examples certain frequently occurring methods will be referenced by shorthand phrases.

Plasmids are designated by a small p proceeded and/or followed by capital letters and/or numbers. The starting plasmids herein are commercially available, are available on an unrestricted basis, or can be constructed from such available plasmids in accord with published procedures.

"Klenow treatment" refers to the process of filling a recessed 3' end of double stranded DNA with deoxyribonucleotides complementary to the nucleotides making up the protruding 5' end of the DNA strand. This process is usually used to fill in a recessed end resulting from a restriction enzyme cleavage of DNA. This creates a blunt or flush end, as may be required for further ligations. Treatment with Klenow is accomplished by reacting (generally for 15 minutes at 15° C.) the appropriate complementary deoxyribonucleotides with the DNA to be filled in under the catalytic activity (usually 10 units) of the Klenow fragment of *E. coli* DNA polymerase I ("Klenow"). Klenow and the other reagents needed are commercially available. The procedure has been published extensively. See for example T. Maniatis, et al., (1982) Molecular Cloning, pp. 107–108.

"Digestion" of DNA refers to catalytic cleavage of the DNA with an enzyme that acts only at certain locations in the DNA. Such enzymes are called restriction enzymes, and the sites for which each is specific is called a restriction site. "Partial" digestion refers to incomplete digestion by restriction enzyme, i.e., conditions are chosen that result in cleavage of some but not all of the sites for a given restriction endonuclease in a DNA substrate. The various restriction enzymes used herein are commercially available and their reaction conditions, cofactors and other requirements as established by the enzyme suppliers were used. Restriction enzymes commonly are designated by abbreviations composed of a capital letter followed by other letters and then, generally, a number representing the microorganism from which each restriction enzyme originally was obtained. In general, about 1 μg of plasmid or DNA gragment is used with about 1 unit of enzyme in about 20 μl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis, et al., Id., pp. 133–134).

"Recovery" or "isolation" of a given fragment of DNA from a restriction digest means separation of the digest on 6 percent polyacrylamide gel electrophoresis, identification of the fragment of interest by molecular weight (using DNA fragments of known molecular weight as markers), removal of the gel section containing the desired fragment, and separation of the gel from DNA. This procedure is known generally. For example, see R. Lawn, et al., (1981) Nucleic Acids Res. 9, 6103–6114, and D. Goeddel, et al., (1980) Nucleic Acids Res. 8, 4057.

"Southern Analysis" is a method by which the presence of DNA sequences in a digest or DNA-containing composition is confirmed by hybridization to a known, labelled oligonucleotide or DNA fragment. For the purposes herein, Southern analysis shall mean separation of digests on 1 percent agarose and depurination as described by G. Wahl, et al., (1979) Proc. Nat. Acad. Sci. U.S.A. 76, 3683–3687, transfer to nitrocellulose by the method of Southern, E. (1975) J. Mol. Biol. 98, 503–517, and hybridization as described by T. Maniatis, et al., (1978) Cell 15, 687–701.

"Transformation" means introducing DNA into an organism so that the DNA is replicable, either as an extrachromosomal element or chromosomal integrant. Unless otherwise stated, the method used herein for transformation of *E. coli* is the $CaCl_2$ method of Mandel, et al., (1970) J. Mol. Biol. 53, 154, and for Bacillus, the method of Anagnostopolous, et al., (1961) J. Bacteriol. 81, 791–746.

"Ligation" refers to the process of forming phosphodiester bonds between two double stranded nucleic acid fragments (T. Maniatis, et al., Id., p. 146). Unless otherwise stated, ligation was accomplished using known buffers and conditions with 10 units of T4 DNA ligase ("ligase") per 0.5 μg of approximately equimolar amounts of the DNA fragments to be ligated. Plasmids from the transformants were prepared, analyzed by restriction mapping and/or sequenced by the method of Messing, et al., (1981) Nucleic Acids Res. 9, 309.

"Preparation" of DNA from transformants means isolating plasmid DNA from microbial culture. Unless otherwise stated, the alkaline/SDS method of Maniatis, et al., Id., p. 90, was used.

"Oligonucleotides" are short length single or double stranded polydeoxynucleotides which were chemically synthesized by the method of Crea, et al., (1980) Nucleic Acids Res. 8, 2331–2348 (except that mesitylene nitrotriazole was used as a condensing agent) and then purified on polyacrylamide gels.

All literature citations are expressly incorporated by reference.

EXAMPLE 1

Site-specific mutagenesis of the *B. amyloliquefaciens* subtilisin gene at position 221; preparation of the gene for cassette insertion The construction of pS4 is described in detail in EPO Publication No. 0130756. This plasmid is depicted in FIG. 4. pS4 contains 4.5 kb of sequence derived from pBS42 (solid line) and 4.4kb of sequence containing the *B. amyloliquefaciens* subtilisin gene and flanking sequences (dashed line). pBS42 was constructed as described in EPO Publication No. 0130756 and Band, L. and Henner, D. J. (1984) DNA 3, 17–21. It was digested with BamHI and ligated with Sau3A partially digested chromosomal DNA from *B. amyloliquefaciens* (ATCC No. 23844) as described in EPO Publication No. 0120756. pS4 was selected from this genomic library.

pS4-5, a derivative of pS4 made according to Wells, et al. (1983) Nucleic Acids Res. 11, 7911–7924, was digested with EcoRI and BamHI, and the 1.5 kb EcoRI-BamHI fragment recovered. This fragment was ligated into replicative form M-13 mp9 which had been digested with EcoRI and BamHI (Sanger, et al., (1980) J. Mol. Biol. 143, 161–178; Messing, et al., (1981) Nucleic Acids Res. 9, 304–321; Messing, J. and Vieira, J. (1982) Gene 19, 269–276). The M-13 mp9 phage ligations, designated M-13 mp9 SUBT, were used to transform *E. coli* strain JM101 (ATCC 33876) and single stranded phage DNA was prepared from a two mL overnight culture. An oligonucleotide primer was synthesized having the sequence

5'-GTACAACGGTACCTCACGCACGCT-
GCAGGAGCGGCTGC-3'.

This primer conforms to the sequence of the subtilisin gene fragment encoding amino acids 216–232 except that the 10 bp of codons for amino acids 222–225 were deleted, and the codons for amino acids 220, 227 and 228 were mutated to introduce a KpnI site 5' to the Ser-221 codon and a PstI site 3' to the Ser-221 codon. See FIG. 5. Substituted nucleotides are denoted by asterisks, the underlined codons in line 2 represent the new restriction sites and the scored sequence in line 4 represents the inserted oligonucleotide. The primer (about 15 μM) was labelled with [$^{32}$p] by incubation with [$\gamma^{32}$p]-ATP (10 μL in 20 μL reaction)(Amersham 5000 Ci/mmol, 10218) and T$_4$ polynucleotide kinase (10 units) followed by non-radioactive ATP (100 μM) to allow complete phosphorylation of the mutagenesis primer. The kinase was inactivated by heating the phosphorylation mixture to 68° C. for 15 minutes.

The primer was hybridized to M-13 mp9 SUBT as modified from Norris, et al., (1983) Nucleic Acids Res. 11, 5103–5112 by combining 5 μL of the labelled mutagenesis primer (~3 μM), ~1 μg M-13 mp9 SUBT template, 1 μL of 1 μM M-13 sequencing primer (17-mer), and 2.5 μL of buffer (0.3 M Tris pH 8, 40 mM MgCl$_2$, 12 mM EDTA, 10 mM DTT, 0.5 mg/ml BSA). The mixture was heated to 68° C. for 10 minutes and cooled 10 minutes at room temperature. To the annealing mixture was added 3.6 μL of 0.25 mM dGTP, dCTP, dATP, and dTTP, 1.25 μof 10 mM ATP, 1 μL ligase (4 units) and 1 μL Klenow (5 units). The primer extension and ligation reaction (total volume 25 μl) proceeded 2 hours at 14° C. The Klenow and ligase were inactivated by heating to 68° C. for 20 minutes. The heated reaction mixture was digested with BamH1 and EcoRI and an aliquot of the digest was applied to a 6 percent polyacrylamide gel and radioactive fragments were visualized by autoradiography. This showed the [$^{32}$p] mutagenesis primer had indeed been incorporated into the EcoRI-BamH1 fragment containing the now mutated subtilisin gene.

The remainder of the digested reaction mixture was diluted to 200 μL with 10 mM Tris, pH 8, containing 1 mM EDTA, extracted once with a 1:1 (v:v) phenol/chloroform mixture, then once with chloroform, and the aqueous phase recovered. 15 μL of 5 M ammonium acetate (pH 8) was added along with two volumes of ethanol to precipitate the DNA from the aqueous phase. The DNA was pelleted by centrifugation for five minutes in a microfuge and the supernatant was discarded. 300 μL of 70 percent ethanol was added to wash the DNA pellet, the wash was discarded and the pellet lyophilized.

pBS42 was digested with BamHl and EcoRI and purified on an acrylamide gel to recover the vector. 0.5 μg of the digested vector, 0.1 μg of the above primer mutated EcoRI-BamHI digested subtilisin genomic fragment, 50 μM ATP and 6 units ligase were dissolved in 20 μl of ligation buffer. The ligation went overnight at 14° C. The DNA was transformed into *E. coli* 294 rec+ (ATCC 31446) and the transformants grown in 4 ml of LB medium containing 12.5 μg/ml chloramphenicol. Plasmid DNA was prepared from this culture and digested with KpnI, EcoRI and BamHI. Analysis of the restriction fragments showed 30–50 percent of the molecules contained the expected KpnI site programmed by the mutagenesis primer. It was hypothesized that the plasmid population not including the KpnI site resulted from M-13 replication before bacterial repair of the mutagenesis site, thus producing a heterogenous population of KpnI+ abd KpnI− plasmids in some of the transformants. In order to obtain a pure culture of the KpnI+ plasmid, the DNA was transformed a second time into *E. coli* to clone plasmids containing the new KpnI site. DNA was prepared from 16 such transformants and six were found to contain the expected KpnI site.

Preparative amounts of DNA were made from one of these six transformants (designated pΔ221) and restriction analysis confirmed the presence and location of the expected KpnI and PstI sites. 40 μg of pΔ221 were digested in 300 μL of KpnI buffer plus 30 μL KpnI (300 units) for 1.5 h at 37° C. The DNA was precipitated with ethanol, washed with 70 percent ethanol, and lyophilized. The DNA pellet was taken up in 200 μL HindIII buffer and digested with 20 μL (500 units) PstI for 1.5 h at 37° C. The aqueous phase was extracted with phenol/CHCl$_3$ and the DNA precipitated with ethanol. The DNA was dissolved in water and purified by polyacrylamide gel electrophoresis. Following electroelution of the vector band (120 v for 2 h at 0° C. in 0.1× TBE (Maniatis, et al., Id.)) the DNA was purified by phenol/CHCl$_3$ extraction, ethanol precipitation and ethanol washing.

Although pΔ221 could be digested to completion (>98 percent) by either KnpI or PstI separately, exhaustive double digestion was incomplete (<<50 percent). This may have resulted from the fact that these sites were so close (10 bp) that digestion by KnpI allowed "breathing" of the DNA in the vicinity of the PstI site, i.e., strand separation or fraying. Since PstI will only cleave double stranded DNA, strand separation could inhibit subsequent PstI digestion.

EXAMPLE 2

Ligation of oligonucleotide casette Ser221→Ala into the subtilisin gene

10 μM of the complementary oligonucleotides (under and overscored in FIG. 5), which were not 5' phosphorylated were annealed in 20 μl ligase buffer by heating for five minutes at 68° C. and then cooling for 15 minutes at room temperature. 1 μM of the annealed oligonucleotide encoding the substitution of alanine for serine 221, ~0.2 μg KpnI and PstI digested pΔ221 obtained in Example 1, 0.5 mM ATP, ligase buffer and 6 units T$_4$ DNA ligase in 20 μL total volume was reacted overnight at 14° C. to ligate the Ser(221)→Ala cassette in the vector. A large excess of cassette (~300× over the pΔ221 ends) was used in the ligation to help prevent intramolecular KpnI-KpnI ligation. The reaction was diluted by adding 25 μL of 10 mM Tris pH 8 containing 1 mM EDTA. The mixture was reannealed to avoid possible cassette concatemer formation by heating to 69° C. fo five minutes and cooling for 15 minutes at room temperature. The ligation mixture was transformed into *E. coli* 294 rec+ cells. A small aliquot from the transformation mixture was plated to determine the number of independent transformants. The large number of transformants indicated a high probability of multiple mutagenesis. The rest of the transformants (~200–400 transformants) were cultured in 4 ml of LB medium plus 12.5 μg chloramphenicol/ml. DNA was prepared from each transformant. This DNA was digested with KpnI. Approximately 0.1 μg was used to retransform *E. coli* rec+ and the mixture was plated to isolate individual colonies. Since ligation of the Ser22-1→Ala cassette into the gene and bacterial repair upon transformation destroyed the KpnI and PstI sites, only pΔ221 was cut when the transformant DNA was digested with KpnI. This linearized plasmid thus would have a much lower transformation efficiency than the circular plasmid containing the Ser221→Ala cassette. Individual transformants were grown in culture and DNA was prepared for direct plasmid sequencing. A synthetic oligonucleotide primer having the sequence 5'-GAGCTTGATGTCATGGC-3' was used to prime the dideoxy sequencing reaction. The sequence obtained corresponded to that expected for the substitution of alanine for serine at residue 221. This plasmid, pAla+221, encoded the mutant subtilisin designated A221 or Ser221→Ala.

EXAMPLE 3

Site-Directed Mutagenesis of *B. amyloliquefaciens* subtilisin gene at position 32

Three hydrogen bonds have been proposed that may help stabilize the transition state of the subtilisinsubstrate complex. (For example, see Kossiakoff, A. A. (1985) in *Biological Macromolecules and Assemblies*, Vol. III, in press.) One of these hydrogen bonds is between the aspartic acid at residue 32 and the positivity charged histidine at position 64. Kossiakoff, A. A. and Spencer, S. A. (1981) Biochem. 20, 6462–6474. The second involves a hydrogen bond between the scissile amide nitrogen of the substrate and the proton of histidine 64. A third set of hydrogen bonds forms between the enzyme and the oxyanion that is produced from the carbonyl oxygen of the substrate. Crystallographic studies of subtilisin show that two hydrogen bonds are formed with the substrate oxyanion: one hydrogen bond being from the catalytic serine at residue 221 while the other is from asparagine at residue 155. Robertus, J. D., Kraut, J., Alden, R. A. and Birktoft, J. J. (1972) Biochem. 11, 4293–4303; Matthews, D. A., Alden, R. A., Birktoft, J. J., Freer, S. T. and Kraut, J. (1975) J. Biol. Chem. 250, 7120–7126; and Poulos, T. L., Alden, R. A., Freer, S. T., Birktoft, J. J. and Kraut, J. (1976) J. Biol. Chem. 250, 1097–1103. In this example site-directed mutagenesis of Asp32→Asn was undertaken to determine the effect of such substitution on catalytic activity.

pS4–5 was digested with EcoRI and BamHI, and the 1.5 kb EcoRI-BamHI fragment recovered. This fragment was ligated into replicative form M-13 mpII which had been digested with EcoRI and BamHI. This vector was designated M13mpII SUBT and single-stranded phage DNA was prepared from it. Sanger, et al., (1980) J. Mol. Biol. 143, 161–178; Messing, et al., (1981) Nucleic Acids Res. 9, 304–321; Messing, J. and Vieira, J. (1982) Gene 19, 269–276. An oligonucleotide primer was synthesized having the sequence:

5'-CGGTTATCAACAGCGGTAT-3'.

This primer includes the sequence of the subtilisin gene fragment encoding amino acids 30–34 except that the codon for amino acid 32 was changed from GAC (aspartic acid) to AAC (asparagine). The single stranded M13mpII SUBT DNA was primed with the 5'-phosphorylated M13 sequencing primer and the mutagenesis primer, as previously described. Adelman, J. P., Hayflick, J. S., Vasser, M. and Seeburg, P. H. (1983) DNA 2, 183–193. Mutant phage were identified by hybridization with the 32P-mutagenic primer using a tetramethyl ammonium chloride washing procedure. Wood, W. I., Gitschier, J., Lasky, L. A. and Lawn, R. M. (1985) Proc. Natl. Acad. Sci. U.S.A. 82, 1585–1588. All mutations were confirmed by M13 dideoxy sequencing. Sanger, F., Coulson, A. R., Barrell, B. G., Smith, A. J. H. and Roe, B. A. (1980) J. Mol. Biol. 143, 161–178. The mutagenized 1.5 kb EcoRI-BamHI fragment was sub-cloned into the *E. coli-B. subtilis* shuttle plasmid, pBS42. This plasmid was designated pAsn+32 and was used to transform *E. coli* 294rec+. Mandel, M., et al. (1970) J. Mol. Biol. 53, 159–162. The mutant subtilisin encoded by this plasmid was designated N32 or Asp+32→Asn. To ensure that no second site mutation(s) had occurred, the region of DNA that was sequenced was replaced with wild type sequence containing Asp+32. This reconstruction restored the wild type protease phenotype.

EXAMPLE 4

Site-Directed mutagenesis of the *B. amyloliquefaciens* subtilisin gene by deletion of carboxyl terminal residues containing Ser221

The procedure of Example 3 was followed in substantial detail. In this example, a primer having the sequence

5'-AAGGCACTTCCGGGAGCTCAACCCGG-GTAAATACCCT-3' directed a 7 bp deletion and a frame-shift starting at codon 163 giving rise to the plasmid pΔ66. This frame shift causes premature chain termination 21 codons downstream. The mutant subtilisin encoded by this plasmid was designated Δ166.

Plasmid pΔ66 was transformed into *E. coli* strain 294 rec+ as described by Mandel, M. and Higs, A. (1970) J. Mol. Biol. 53, 159–162. Plasmid DNA prepared from transformed *E. coli* 294 rec+ was used to transform various *B. subtilis* hosts as described hereinafter.

EXAMPLE 5

Site directed mutagenesis of *B. amyloliquefaciens* subtilisin gene by deletion of amino acid residues in the signal sequence The procedure of Example 3 again was followed except that a primer having the sequence

5'-GAGAGGCAAAAAGCTTTTTGCTTTAGC-3' was used. This primer directed an in-frame deletion of codons −102 to −98 in the subtilisin signal sequence. This mutant DNA sequence when subcloned into pBS42 was designated pΔ(−102). The mutant subtilisin was designated Δ(−102).

The plasmids and polypeptides encoded by pS4–5 and the mutated plasmids of Examples 3, 4 and 5 are shown in FIG. 6.

EXAMPLE 6

Site-Directed mutagenesis of *B. amyloliquefaciens* subtilisin gene at position 48

The procedure of Example 3 again was followed in substantial detail to produce a mutant subtilisin containing the substitution of arginine for the alanine at position 48. In this example, mutagenesis of Ala48→Arg was directed by a 26-mer oligonucleotide having the sequence:

5'-GTAGCAGGCGGACGCTCCATGGTTCC-3'

The primer included the sequence of the subtilisin gene fragment encoding amino acids 44 through 52 except that the codon normally encoding alanine was substituted with the codon CGC encoding arginine; the serine codon at 49(AGC) was also converted to TCC to introduce a convenient NcoI site. The plasmid containing this mutation after subcloning into pBS42 was designated pAla48→Arg and was used to transform E. coli 294 rec+. The mutant subtilisin encoded by this plasmid was designated R48 or Ala48→Arg and was used to transform various species of B. subtilis.

EXAMPLE 7

Cell fractions and Western Blot analysis

Stationary phase cultures of various strains of B. subtilis transformed with pBS42, pAsn+32 or pΔ166 in LB medium containing 1.25 μg/ml chloramphenicol (1.25 ml) were treated with 1mM PMSF to inactivate subtilisin activity. Samples were centrifuged at 11,000×g for 10 minutes and a medium fraction of 0.6 ml was mixed with 0.6 ml 20 percent trichloroacetic acid. The suspension was incubated at 4° C. for 30 minutes and the precipitated protein was recovered by centrifugation for 10 minutes at 19000 rpm in a Sorvall SS34 rotor (37,000×g). After washing with 0.6 ml acetone followed by centrifugation, the pellet was dried. The sample was disassociated in NaDodSO$_4$ sample buffer (4 percent glycerol, 2 percent NaDodSO$_4$ and 10mM Na phosphate, pH 6.8) at 95° C. for 3 minutes. A modified cell fractionation procedure was employed Kaback, H. R. (1971) Methods in Enzymology, ed. Jakoby, W. B., Acad. Press, N.Y., Vol. 22, pp. 99–120. The cell pellet was washed with 100 μl of 10 mM Tris-HCl, pH 7.4, treated with PMSF as before and centrifuged. The cells were resuspended in 100 μl of 30 mM Tris-HCl, pH 8.0 and treated with 20 μg/ml T4 lysozyme at 37° C. for 20 minutes. After centrifugation at 40,000×g for 20 minutes, the supernatant (i.e., cytosol fraction) was saved. The pellet (i.e., crude membrane fraction) was resuspended in 100 μl of 50 mM Na phosphate, pH 6.6 and treated with 5 mM EDTA. The crude membrane fraction was treated with 10 μg/ml DNAse, 10 mM MgCl$_2$, and incubated at 37° C. for 10 minutes. The membranes were recovered by centrifugation at 40,000×g for 20 minutes, washed once in 100 μl of 50 mM sodium phosphate buffer and disassociated as described above.

The samples were electrophoresed on 12.5 percent polyacrylamide gels (0.75 mm×15 cm×15 cm) as described by Laemmli (Laemmli, U.K. (1970) Nature 227, 680–685; Laemmli, U. K. and Favre, M. (1973) J. Mol. Biol. 80, 575–599) except that 10 percent glycerol was added to the separating gel to enable simultaneous casting and polymerization with the stacking gel. For greater resolution, particular samples were electrophoresed in 10 percent polyacrylamide gels (0.4 mm×50 cm). The polyacrylamide gels were transferred to nitrocellulose treated with 10 percent acetic acid, neutralized, and probed with $^{125}$I labelled antibodies to B. amyloliquefaciens subtilisin. Towbin, H., Stdaehelin, T. and Gordon, J. (1979) Proc. Natl. Acad. Sci. U.S.A. 76, 4350–4354.

EXAMPLE 8

Preparation of antibodies and radioimmunoassay

B. amyloliquefaciens subtilisin was purified (Philipp, M. and Bender, M. L. (1983) Mol. Cell. Biochem. 51, 5–32) and digested with 100 mg/ml CNBr (5 mg/ml protein) in 88 percent formic acid. After incubation at room temperature for 2 hours, the reaction mixture was lyophilized and resuspended in 0.1 M Tris-HCl, pH 8.0 containing 0.05 percent Triton X-100. This was mixed with an equal volume of complete Freund's adjuvant and distributed intracutaneously (1 mg/animal) over several sites on New Zealand white-female rabbits. Booster injections were given in the ear vein (200 μg/animal) on days 21 and 42. Bleeds were collected weekly following each boost.

Subtilisin antigens in the membrane, media, and cytosol fractions were quantitated by radioimmunoassay. The membrane fractions were treated with 5M urea prior to analysis in order to solubilize the antigen. The urea extract was diluted 1:20 with assay buffer (10 mM Na phosphate, pH 7.4, 0.9 percent NaCl, 0.5 percent bovine serum albumin and 1 mM PMSF) just before analysis. Affinity purified anti-subtilisin immunoglobulin fraction (Eveleigh, J. W. and Levy, D. E. (1977) J. Solid-Phase Biochem. 2, 45–78) was coated at 10 μg/ml onto the 96 well microtiter plate for 2 hours at room temperature. After washing with assay buffer, samples and standards were incubated in the wells as before. After washing, 100,000 cpm of $^{125}$I-antibody was introduced and the plate incubated again for 2 hours. After washing, the plate was counted.

EXAMPLE 9

Expression and secretion of wild type B. amyloliquefaciens subtilisin

The wild type B. amyloliquefaciens subtilisin gene was introduced on the plasmid, pS4-5 into B. subtilis strain BG2036. The construction of this strain is described in detail in EPO Publication 0130756. In this strain both the endogenous alkaline protease (apr) (i.e., subtilisin) and neutral protease (npr) genes have been deleted (Yang, M. Y., Ferrari, E. and Henner, D. J. (1984) J. Bacteriol. 160, 15–21). FIG. 7 shows the Western blot analysis of media (a) and membrane (b) fractions sampled as a function time of culture growth. Numbers 1–5 refer to time points of 4.8, 6.5, 7.8, 10.8 and 24 h, respectively. ST denotes 0.1 μg of a standard mature B. amyloliquefaciens subtilisin (P27). The band appearing in the media below P27 is a degradation product of P27. A sample containing 0.3 ml equivalents of culture for medium samples or 0.2 ml equivalents of culture for membrane samples was loaded onto the gels shown.

This Western analysis shows that at both early and late stages of cell growth only the 27,000 dalton mature form of subtilisin (P27) was detected in media fractions. In contrast, analyses of membrane fractions shows the presence of a 42,000 dalton precursor (P42). Initially, the appearance of P42 in the membrane was coincident with the appearance of P27 in the medium. Subsequently, P42 was seen to disappear as P27 accumulated.

FIG. 8 shows the time course of cell growth (+), secretion of mature subtilisin (P27) into the medium (x), and accumulation of subtilisin precursor (P42) into cell membrane fractions (Δ). Cell growth was measured by absorbance at 550nm while subtilisin was quantified by radioimmunoassay. Values were normalized to their maxima (cell growth was $A_{550}$=4; mature subtilisin (P27) was 36 μg/ml; and the precursor (P42) was 0.06 μg/ml). The accumulation of P42 measured by this RIA peaked at approximately 6.5 h of cell growth which was just prior to the expected onset of sporulation. As the cells sporulated, as measured by the drop in absorbance at 550 nm, P27 continued to accumulate in the media at the expense of P42 in the membrane. Thus, wild type subtilisin can be detected in both the membrane of the expression host and media supporting the same shortly after the media is innoculated.

EXAMPLE 10

Non-secretion of certain mutant subtilisins

*B. subtilis* BG2036 was transformed separately with pAsn+32 and pΔ66 and grown for 20 hours. Cells were fractionated into membrane and media components, and fractions were loaded onto gels as previously described in Example 7. The results are shown in FIG. 9. ST denotes a gel lane containing 0.1 μg of subtilisin. The media membrane fractions in tracks 1 to 4 were derived from pS4-5, pAsn+32, pΔ66 and the vector control, pBS42, respectively.

Mature subtilisin (P27) was not observed in the medium for pAsn+32. Initially, the precursor of Asn+32, P42, appeared in the membrane with normal synthesis kinetics (data not shown). However, unlike the wild-type precursor, it continued to accumulate reaching a plateau late in stationary phase. The Asn+32 precursor migrated roughly 1,000 daltons smaller in size than the Asp+32 precursor. This is presumably due to charge and not a size difference as similar differences have been observed between basic and acidic substitutions in other subtilisin positions.

In pΔ166, the region of the gene coding for the carboxy-terminus of the protein was deleted thereby removing the catalytic serine+221 which is required for subtilisin activity. As can be seen in FIG. 9, subcellular fractions of stationary phase cells expressing pΔ66 showed only a 31,000 dalton membrane bound antigen (P31). The difference in electrophoretic migration observed for P31 and P42 was consistent with the length of the pΔ66 deletion. Immunologically reactive mutant subtilisin was not observed in the media fraction.

EXAMPLE 11

Membrane bound P42 contains the subtilisin signal sequence

To determine whether the membrane bound precursor, P42, contained the signal sequence, a deletion of five residues, −102 through −98, was constructed in the subtilisin gene (pΔ-102). FIG. 10 is the high resolution (50 cm) Western blot analysis of membrane bound precursors from wild type (pS4–5) and the signal peptide deletion mutant pΔ-102. Lane 1 contains 0.1 μg of mature subtilisin; lanes 2 and 4 contain membrane fractions from a pΔ-102 culture of *B. subtilis*, BG2036; lane 3 contains membranes from a wild type subtilisin (pS4-5) culture of *B. subtilis*, BG2036. This Western analysis revealed an alteration in the electrophoretic mobility of the translated precursor for pΔ-102 consistent with a five amino acid deletion, indicating that the membrane precursor P42 from pAsn+32 probably also contains the subtilisin signal sequence.

EXAMPLE 12

Maturation of membrane bound mutant subtilisin

In contrast to the wild-type subtilisin, the maturation of the Asn+32 mutant was blocked when produced in *B. subtilis* BG2036 which lacked both subtilisin (apr) and neutral protease (npr) genes. To test whether enzymatically active subtilisin or neutral protease was necessary for processing, pAsn+32 was expressed in various *B. subtilis* hosts. FIG. 11 shows the Western analysis of medium fractions (lanes a and A) and membrane fractions (lanes b and B) from *B. subtilis* cultures containing either the pAsn+32 plasmid (lanes A and B) or the vector, pBS42, minus the subtilisin gene (lanes a and b). These plasmids were expressed in the following *B. subtilis* strains which have been described by Stahl, M. L. and Ferrari, E. (1984) J. Bacteriol. 158, 411–418 and Yang, M. Y., et al. (1984) J. Bacteriol 160, 15–21: *B. subtilis* I-168 (apr+ npr+), *B. subtilis* BG2044 (apr+ npr−), *B. subtilis* BG2019 (apr− npr+), and *B. subtilis* BG2036 (apr− npr+). Cultures were grown and fractionated as previously described. As can be seen, processing of the membrane bound precursor to the mature Asn+32 enzyme was only observed in apr(+) hosts. Maturation of Asn+32 subtilisin was independent of an intact npr gene as shown by the continued presence of P42 in the apr− npr+ strain, BG2019. It should be noted that antibodies elicited by the *B. amyloliquefaciens* subtilisin do not cross-react with the *B. subtilis* subtilisin. Thus, a P27 band was not seen with the vector control, pBS42, in the apr+ hosts.

EXAMPLE 13

In vitro removal of a membrane bound mutant subtilisin

The P42 precursor of Asn+32 subtilisin derived from the apr− npr− host, BG2036, can also be matured in vitro by addition of subtilisin to *B. subtilis* BG2036 transformed with pAsn+32. Cell pellets were treated with exogenous subtilisin in vitro prior to analysis. Cells from 12.5 ml of a stationary phase (16 hour) culture were resuspended in 1.0 ml of osmotically supported Tris buffer (30 mM Tris-HCl, 25 percent (w/v) sucrose, pH 8.0) and treated with 1 μg/ml *B. licheniformis* subtilisin (Sigma). After overnight incubation at room temperature with stirring, the cells and medium were separated by centrifugation and fractionated as described above.

FIG. 12 shows the Western analysis of *B. subtilis* BG2036 cells containing pAsn+32 (lanes labeled b) or vector pBS42 (lanes labeled a) plasmids. Medium and membrane fractions are shown for samples taken immediately after cultruing (labeled 0) or after overnight incubation in the presence (labeled +sbt) or absence (labeled −sbt) of 1 μg/ml *B. licheniformis* subtilisin. As can be seen, the majority of the P42 material was released from the membrane and converted to P27. The *B. licheniformis* enzyme was used because *B. amyloliquefaciens* subtilisin antibodies do not cross-react with it. In contrast, cells incubated in the absence of protease showed neither accumulation of P27 nor loss of P42. Cells containing only the vector plasmid, pBS42, did not show any detectable P27 in the presence of added *B. licheniformis* subtilisin. These studies suggest that P42 and P27 have a precursor-product relationship.

EXAMPLE 14

Removal of membrane bound mutant subtilisin by co-culturing

In addition to the in vitro method, it is also possible to mature an inactive subtilisin by co-culturing a strain possessing the inactive protein with a strain carrying a plasmid copy of an active endoprotease. For clarity and detection purposes, the active gene chosen was *B. amyloliquifaciens* subtilisin with the substitution Ala48-→Arg prepared as described in Example 6. This latter enzyme migrates much faster on SDS gels than the normal wild type or the inactive mutant Ser221→Ala221 used in this experiment. Plasmids pAla+221 and pArg+48 were separately transformed into the BG2036 host which lacks both alkaline and neutral protease.

Strains were precultured to a cell density of ~0.5 A550/ml (log phase) and then fresh flasks were innoculated (1:100) such that equal cell densities were introduced into each flask. Samples were innoculated as ratios of R48 (Arg+48) cells to A221 (Ala+221) cells as follows: (1) 1:0, (2) 0:1, (3) 0.5:0.5, (4) 0.25:0.75, (5) 0.1:0.9, and a final flask (6) of the vector control pBS42. Cultures were then grown to stationary phase, and the cells removed by centrifugation at 11,000× g for 10 minutes in a Sorvall SS34 rotor. 600 μl samples of the media were treated with an equal volume of 20% TCA and the pellets collected by centrifugation at 19000 rpm in a Sorvall SS34 rotor (4° C.). After washing with 600 μl of acetone and centrifugation as before, the pellets were dried in a SpeedVac and then dissociated in SDS sample buffer (25 μl percent glycerol, 2 percent SDS, 10 mM Na phosphate pH 6.8) at 95° C. for 3 minutes. Samples were electrophoesed on 50 cm, 12.5 percent gels as described.

FIG. 13 depicts the electrophoretic pattern of media samples as detected by Coumassie Blue staining. As shown therein, the band corresponding to A221 subtilisin is clearly resolved from the R48 subtilisin. Even in the presence of low amounts of R48 cells, the production of A221 is significantly enhanced over the control A221 containing cells grown in the absence of active enzyme. Thus, active enzyme secreted by co-cultured cells is capable of maturing inactive subtilisin expressed by another strain which is incapable of secreting enzymatically active endoprotease.

EXAMPLE 15

Binding of a mutant subtilisin (Ser221→Ala) to subtilisin inhibitor

To test the binding of the catalytically inactive mutant of wild type subtilisin, A221, to a subtilisin inhibitor, turkey ovomucoid third domain (TOM3) was utilized. Upon incubation with TOM3, the wild type enzyme binds the inhibitor leading to a quantitative decrease in activity.

Wild type subtilisin (1.07×10−5 M) was incubated with TOM3 (0.09×10-5 M) in the presence or absence of A221 enzyme (1.67×10-5 M). Activity was measured on the succinyl-Ala-Ala-Pro-Phe-pNa substrate. Results were as follows:

TABLE 1

| Solution | Activity total | (units) bound to TOM3 |
|---|---|---|
| WT | .896 | 0 |
| WT + TOM3 | .143 | .753 |
| WT + TOM3 + A221 | .430 | .466 |

As shown in Table 1, the competitive binding of A221 to TOM3 inhibitor causes a 38 percent reduction in the binding of the wild type enzyme to the inhibitor. Therefore, although the A221 mutant is catalytically inactive, it is still capable of binding a subtilisin inhibitor.

EXAMPLE 16

Construction of a thermolabile mutant subtilisin

A thermolabile mutant subtilisin was prepared containing the substitution of methionine at position 222 with aspartic acid (Met222→Asp or D222) as described in EPO Publication No. 0130756.

This particular mutant is thermolabile as demonstrated by the approximate 90% decrease in its enzymatic activity on skim milk plates at 45° C. versus 37° C. when compared to wild type subtilisin or other mutants of subtilisin at position 222.

EXAMPLE 17

Thermal inactivation of enzymatically active endoprotease after maturation of subtilisin Ser221→Ala In Example 14, the Ser221→Ala mutant was matured by coculturing with Ala48→Arg. In this example, the experiment was repeated, this time using the thermolabile, Met222→D222 mutant subtilisin of Example 16 as the active enzyme. In this example B. subtilis BG2036, transformed separately with pD222 and pA221, were co-cultured at a ratio of 1(D222):9(A221). A control coculture of D222 transformed B. subtilis BG2036 and untransformed BG2036 at the same ratio was similarly treated. At the conclusion of growth the media was treated at 50° C. for up to 15 minutes. As shown in FIG. 14, essentially all of the activity of the D222 subtilisin in the coculturing experiment was eliminated after 15 minutes while only 10% of the enzyme detectable on SDS gels was lost. Under these conditions, which are similar to those in Example 14 (except that the D222 subtilisin co-migrates with the A221 subtilisin), only 10% of the material would be expected to be the D222 enzyme. Thus, the Ser221→Ala mutant was produced by co-culturing with the thermolabile Met222→D222 mutant and the active enzyme removed by a simple heat step.

EXAMPLE 18

Cleavage of prosubtilisin hGH fusion polypeptide with subtilisin to generate mature hGH pPA422 is an expression plasmid designed to secrete human growth hormone (hGH) in *Bacillus subtilis*. The plasmid replicates in *E. coli* as an extra chromosomal element but can only integrate into the *Bacillus subtilis* chromosome at the Trp region. The integrated plasmid can be amplified to several copies per cell by altering the concentration of chloramphenical in the media. Albertini, A. M. and Galizzi, A. (1985) J. Bact., 162(2), 1203. Transcription of the hGH gene is under the control of the Pac promoter (Yansura, D. G. and Henner, D. J. (1984) Proc. Natl. Acad. Sci. U.S.A., 81, 439) and secretion of hGH is facilitated by the Bacillus amyloliquifaciens amylase signal sequence and 32 amino acids of mature amylase. Cleavage of the secreted fusion protein is made possible by inserting the *Bacillus amyloliquifaciens* subtilisin pro sequence between the partial mature amylase sequence and the hGH gene. Several plasmids were constructed as precursors to the final plasmid PA422.

The plasmid pPA422 was constructed by a three way ligation. The vector was pJH101Trp2 in which the 375 basepair EcoRI-BamHI fragment had been removed. The second piece was a 650 basepair EcoRI-PstI fragment from pPA390 which contained the Pac Promoter and ribosome binding site, amylase signal sequence, 32 codons of mature amylase, codons 45 to 107 of preprosubtilisin, and the first 45 codons of hGH. The third fragment is a 1075 basepair PstI-BamHI fragment from PHGH207. It contains codons 46 to 191 of hGH (Goeddel, D. V., et al. (1979) Nature, 281(5732), 544), followed by the last 180 basepairs of *E. coli* lipoprotein gene (Nakamura, K., et al. (1980) J. Biol. Chem, 255, 210), 100 basepairs 3' of the lipoprotein gene encoding its transcriptional terminator, and finally 346 basepairs of pBR322 between the Hind III and BamHI sites (Bolivar, F., et al. (1977) Gene, 2, 95).

The three fragments, 300 ng of pJH101Trp2 vector and 50 ng of the other two pieces, were ligated in 30 μl with T4DNA ligase. After 3 hours, competent *E. coli* D1210 (ATCC 31449) (Goeddel, D. V., et al. (1979) Proc. Natl. Acad. Sci. U.S.A., 76, 106–110), were transformed with the mixture and plated on LB ampicillin (30 μg/ml) plates. The vectors containing the three fragments of pPA422 were constructed as follows.

pJH101Trp2 pJH101Trp2 was constructed by inserting a 375 basepair Sau3A fragment coding for amino acids 160–276 of the *Bacillus subtilis* Trp E gene (Henner, D. J., et al. (1984) Gene, 34, 169) into the BamHI site of pJH101. Ferrari, F. A., et al. J. Bact., 154(3), 1513. JH101 was digested with BamHI, treated with Bacterial Alkaline Phosphatase, and then ligated to the Trp Sau3A fragment with T4 DNA ligase. Competent *E. coli* strain 294 rec+ was then transformed with the ligation mixture and plated on ampicillin (30 μg/ml) LB plates. Colonies were screened by plasmid isolation (Birnboim, H. C. and Doly, J. (1979) Nucl. Acids Res, 2, 1513) and restriction analysis. One plasmid containing the orientation in which the BamHI site was recreated closest to the EcoRI site was designated pJH101Trp2.

pPA12 pPA12 fuses the Pac promoter and ribosome binding site to the amylase signal sequence. A three piece ligation was used to create the plasmid.

The first piece was the vector pJH101Trp2 in which the 375 basepair EcoRI-BamHI fragment had been removed.

The second piece was an EcoRI blunt fragment which contains the Pac promoter and ribosome binding site and the first two codons of the *Bacillus licheniformis* penicillinase gene. This fragment was created by the "Primer Repair" reaction. Goeddel, D. V., et al. (1980) Nucl. Acids Res., 8, 4057. The primer sequence was TTCATCAAAA and the 175 basepair fragment upon which the primer sat was isolated from an RsaI digest of a pBSA105 subclone. Yansura, D. G. amd Henner, D. H. (1983) Biology and Biotechnology of the Bacilli, eds. Ganesan A. T. and Hoch, J. A. Academic Press, New York. The reaction was subsequently digested with EcoRI to generate the 140 basepair fragment.

The third piece was a 215 basepair blunt BamHI fragment which contains codons 2 through 63 of preamylase (Palva, I., et al. (1981) Gene 15, 43) followed by the following double stranded DNA linker.

5'-TCTAGAATTCATGGCAGAAATAACAAG
AGATCTTAAGTACCGTCTTTATTGTTC-CTAG-5'

The ligation was accomplished by mixing 300 ng pJH101Trp2 vector, and 50 ng of the other two fragments in 30 μl in the presence of T3DNA ligase. After 3 hours competent *E. coli* D1210 (ATCC 31449) were transformed with the mixture and plated on ampicillin (30 μg/ml) LB plates.

pPS11

The plasmid pPS11 was constructed by ligating four fragments. The first was the vector pJH101Trp2 in which the 375 basepair EcoRI BamHI fragment had been removed. The second was a 375 basepair piece obtained by digesting pPS4–5 (Wells, J. A., et al. (1983) Nucl. Acids Res., 11(22), 7911) with EcoRI and AvaI. This piece contains the subtilisin promoter, signal sequence, and 93 codons of preprosubtilisin. Wells, J. A., et al. (1983) Nucl. Acids Res,, 11(22), 7911. The third fragment was a 46 basepair blunt AvaI piece which was generated by digesting pPS4–5 with HinpI followed by treatment with DNA Polymerase Klenow, and then second cutting with AvaI. This fragment codes for amino acids 94 to 108 of preprosubtilisin. The final fragment was a 937 basepair blunt BamHI piece generated by digesting plasmid pHGH207 (Kleid, D. G., et al. EPO Publication No. 0154133 published Sep. 11, 1985) with EcoRI followed by filling in with DNA Polymerase Klenow and second cutting with BamHI.

DPA372

The plasmid pPA372 required four pieces for construction. The first was the vector pJH10Trp2 in which the 375 basepair EcoRI-BamHI fragment had been removed. The second was a 187 basepair EcoRI-HgiAI fragment containing the Pac promoter and ribosome binding site and the first 17 codons of the amylase signal sequence. This was obtained by the appropriate digestion of a pPA12 subclone. The third piece was a 139 basepair HgiAI-EcoRV fragment containing codons 17 to 32 of preamylase. Palva, I., et al. (1981) Gene 15, 43. The last was a 1129 basepair DraI-BamHI pPsll fragment containing codons 45 to 108 of preprosubtilisin followed by an EcoRI linker and the hGH gene. Goeddel, D. V., et al. (1979) Nature, 281(5732) , 544.

The ligation mixture included 300 ng of pJH101Trp2 vector, 200 ng of the DraI-BamHI fragment, and 50 ng of the final two pieces in 30 μl in the presence of T4DNA ligase. After 3 hours competent *E. coli* D1210 was transformed with this mixture and then plated on LB ampicillin plates 30 μg.ml).

pPA390

Plasmid pPA390 was constructed from four pieces. The first was the vector pBR322 (Bolivar, F., et al. (1977) Gene, 2, 95) in which the 748 basepair EcoRIPstI section had been removed. The second was a 496 basepair EcoRI-Sau3A fragment generated by digesting pPA372 completely with EcoRI and partially with Sau3A. This fragment contains the Pac promoter and ribosome binding site, amylase signal sequence, 32 codons of mature amylase and codons 45 to 100 of preprosubtilisin. The third piece was a synthetic DNA duplex with the following sequence.

5'-GATC ACG TAG CAC ATG CGT AC TGC
ATC GTG TAC GCA TG-5'

The fourth piece was a 135 basepair blunt PstI fragment containing the first 45 codons of hGH. (Goeddel, D. V., et al., Nature (1979) 281 (5732), 544.) This fragment was generated by the primer repair reaction. The primer used had the sequence TTC CCA ACT ATA CCA CTA TCT CGTCT ATT and the fragment upon which the primer sat was a 941 basepair XbaI-BamHI fragment from pHGH207.

The primer repair reaction was digested with PstI to generate the 135 basepair fragment.

The four fragments, 300 ng pBR322, 30 ng. EcoRI-Sau3A fragments, 1 μg synthetic DNA duplex, and 5 ng blunt PstI fragment, were ligated in 30 μl with T4 DNA ligase. After 4 hours competent *E. coli* D1210 were transformed with the mixture and then plated on tetracycline LB plates (μg/ml).

Transformation and Amplification

The plasmid pPA422 was used to transform competent Bacillus subtilis strain I-168(TrpC2). Gryczan, T. J., et al. (1978) J. Bacteriol., 134, 318. The transformation mixture was plated on LB plates containing 12.5 μg/ml chloramphenicol. 12 colonies were picked and grown with shaking at 37° C. in 2 YT broth containing 12.5 μg/ml chloramphenicol until 4 hours after the start of stationary phase. All cultures were then centrifuged to remove cells, and the supernatant assayed for hGH by RIA.

The cells from 5 ml of the above cultures which showed the highest level of hGH in the media, were suspended in 300 μl 50 mM glucose, 10 mM EDTA, 25 mM Tris pH 8 containing 4 mg/ml lysozyme. After 30 minutes at 37°, 100 μl of 10 mM Tris 1 mM EDTA were added along with 1 μl 10% SDS. The mixture was then phenol extracted, chloroform extracted, and then 1 ml ethanol added. The cellular DNA was removed, dried, and taken up in 50 μl 10 mM Tris pH 8, 1 mM EDTA.

5 μl of the above cellular DNA was used to transform competent *Bacillus subtilis* BG84 (spoOA−). EPO Publication No. 0130756; Wells, J. A., et al. (1983) Nucl. Acids Res., 11(22), 7911. The transformation mixture was plated on LB plates containing 25 μg/ml chloramphenicol.

Cleavage of Fusion Polypeptide with Subtilisin

*B. subtilis* BG84 containing the plasmid PA 422 was grown in a 10 liter fermenter with yeast extracts and protein hydrolysates to early stationary phase. After removing the cells from the fermentation broth by continuous centrifugation, the clear culture supernatant containing the secreted fusion protein was loaded onto a coupled anti-hGH antibody sepharose GMB column. The fusion protein was eluted from the column into fractions. The fractions containing hGH as measured by hGH RIA activity were pooled for subtilisin cleavage. The reaction mixture for cleavage of the fusion polypeptide contained about 2 μg of antibody purified fusion polypeptide and 16 ng of subtilisin BPN (Albertini, A.M. et al. (1985) *J. Bacteriol.* 162(2), 1203) in 10 mM Tris pH 8.6. The reaction temperature was 25° C. Time points at 1 min. intervals were taken and the reaction was stopped by 15% TCA. The TCA precipitates were washed twice by acetone and finally dissolved in SDS buffer for SDS polyacrylamide gel electrophoresis. The proteins on the gel were transferred onto nitrocellulose paper for immunoblot analysis with anti-hGH antibody. Lanes 1–5 (top) in FIG. 15 represent processing incubation times 0, 0.5, 1, 2 and 4 min., respectively. To the right is indicated the mobility of molecular weight standards of 30,000; 20,000; and 17,000 daltons. To the left is indicated the position of the unprocessed prosubtilisin-hGH fusion (1, the heavy band at 29–30 kd) and the position of mature hGH (2, the lighter band, at 22 kd). The results shown in FIG. 15 indicate that the fusion protein at 29–30 kd was cleaved by subtilisin with the subsequent appearance of a protein at 22 kd (mature hGH).

Having described the preferred embodiments of the present invention, it will appear to those ordinarily skilled in the art that various modifications may be made to the disclosed embodiments, and that such modifications are intended to be within the scope of the present invention.

What is claimed is:

1. A process for producing a subtilisin which has an amino acid substitution in one or more amino acid residues of the catalytic triad of wild-type subtilisin and is incapable of autoproteolytic maturation, wherein said process comprises:
    a) expressing a prepro form of said subtilisin in a host cell and transporting it to the surface of said host cell, wherein said host cell is incapable of releasing said subtilisin from the surface of said host cell, and wherein the prosequence of said prepro form of said subtilisin comprises the prosequence of a subtilisin; and
    b) contacting said host cell with an enzymatically active subtilisin to cleave said subtilisin from said prosequence to release said subtilisin from the surface of said host cell.

2. The process of claim 1 wherein said prepro form of said subtilisin which has an amino acid substitution in one or more amino acid residues of the catalytic triad and is incapable of autoproteolytic maturation contains a signal sequence capable of transporting said subtilisin to the surface of said host cell.

3. The process of claim 2 wherein said signal sequence is the signal sequence of subtilisin.

4. The process of claim 1 wherein said prosequence of said prepro form of said subtilisin which has an amino acid substitution in one or more amino acid residues of the catalytic triad and is incapable of autoproteolytic maturation comprises the prosequence of an enzymatically active subtilisin.

5. The process of claim 1 wherein said contacting is achieved by co-culturing an enzymatically active subtilisin secreting organism with said host cells.

6. The process of claim 1 wherein said contacting is achieved by adding enzymatically active exogenous subtilisin to a culture of said host cells.

7. The process of claim 1 wherein said mutant subtilisin has an amino acid substitution in the catalytic triad at position 221.

8. The process of claim 1 wherein said mutant subtilisin has an amino acid substitution in the catalytic triad at position 32.

9. The process of claim 1 wherein said mutant subtilisin has an amino acid substitution in the catalytic triad at position 64.

10. The process of claim 1 wherein said mutant subtilisin is selected from the group consisting of Ser(221)→AlaΔ166 and Asp(32)→Asn.

11. The process of claim 1 wherein said enzymatically active subtilisin is Ala(48)→Arg.

12. The process of claim 1 wherein said enzymatically active subtilisin is a thermolabile subtilisin.

13. The process of claim 12 wherein said thermolabile subtilisin comprises Met(222)→Asp.

14. The process of claim 12 wherein said host cells comprises *Bacillus subtilis* strains which have the genotype apr−npr−.

15. The process of claim 1 wherein said enzymatically active subtilisin is produced by said host cell.

16. The process of claim 15 wherein said host cells comprise *Bacillus* strains which have the genotype apr−npr+.

17. The process of claim 15 wherein said host cells comprise Bacillus strains which have the genotype apr+npr−.

18. The process of claim 15 wherein said host cells comprise Bacillus strains which have the genotype apr+npr+.

19. A process for producing a polypeptide in a host cell comprising:
  a) producing a fusion polypeptide having an amino-terminal first sequence comprising the prosequence of a subtilisin and a carboxy terminal second sequence comprising a desired polypeptide having a sequence other than that of wild-type subtilisin, wherein said fusion polypeptide is capable of being cleaved by an enzymatically active subtilisin at the junction of said first and second sequences or within said first sequence; and
  b) contacting said fusion polypeptide with said enzymatically active subtilisin to cleave said fusion polypeptide at said junction.

20. The process of claim 19 wherein said contacting step is achieved by co-culturing said host cell and an organism which secretes an enzymatically active subtilisin.

21. The process of claim 19 wherein said desired polypeptide is $\Delta 166$ subtilisin.

22. The process of claim 19 wherein said contacting is achieved by adding enzymatically active exogenous subtilisin to a culture of said host cells.

* * * * *